US007241746B2

(12) United States Patent
Wingrove et al.

(10) Patent No.: US 7,241,746 B2
(45) Date of Patent: Jul. 10, 2007

(54) METHOD AND COMPOSITION FOR TREATING PERIODONTAL DISEASE

(75) Inventors: Frank Wingrove, Ames, IA (US); Rex McKee, Traer, IA (US)

(73) Assignee: Regena Therapeutics, LC, Ames, IA (US)

( * ) Notice: Subject to any disclaimer, the term of this patent is extended or adjusted under 35 U.S.C. 154(b) by 48 days.

(21) Appl. No.: 10/635,144

(22) Filed: Aug. 6, 2003

(65) Prior Publication Data

US 2005/0032720 A1   Feb. 10, 2005

(51) Int. Cl.
   *A61K 31/557* (2006.01)
   *A61K 31/704* (2006.01)
   *A51K 31/65* (2006.01)

(52) U.S. Cl. .......................... 514/152; 514/29; 514/35; 514/36; 514/253.08; 514/573

(58) Field of Classification Search .................. 514/35, 514/152, 253.08, 29, 312, 36, 573
   See application file for complete search history.

(56) References Cited

U.S. PATENT DOCUMENTS

| | | | |
|---|---|---|---|
| 3,965,143 A | 6/1976 | Collins et al. | |
| 4,001,286 A | 1/1977 | Bundy | |
| 4,009,282 A | 2/1977 | Voorhees | |
| 4,025,645 A | 5/1977 | Jelenko, III | |
| 4,113,882 A | 9/1978 | Okazaki et al. | |
| 4,132,738 A | 1/1979 | Kluender et al. | |
| 4,181,725 A | 1/1980 | Voorhees et al. | |
| 4,185,100 A | 1/1980 | Rovee et al. | |
| 4,201,788 A | 5/1980 | Voorhees et al. | |
| 4,254,145 A | 3/1981 | Birnbaum | |
| 4,282,216 A | 8/1981 | Rovee et al. | |
| 4,353,896 A | 10/1982 | Levy | |
| 4,360,518 A | 11/1982 | Rovee et al. | |
| 4,459,310 A | 7/1984 | Dajani | |
| 4,473,565 A | 9/1984 | Rovee et al. | |
| 4,515,810 A | 5/1985 | Chow et al. | |
| 4,707,495 A | 11/1987 | Rosenthale et al. | |
| 4,764,377 A * | 8/1988 | Goodson ..................... 424/435 | |
| 4,840,968 A | 6/1989 | Ohnishi | |
| 4,889,845 A | 12/1989 | Ritter et al. | |
| 4,919,939 A | 4/1990 | Baker | |
| 4,925,873 A | 5/1990 | Friedhoff et al. | |
| 5,015,481 A | 5/1991 | Franz et al. | |
| 5,145,686 A | 9/1992 | Horrobin et al. | |
| 5,167,952 A | 12/1992 | McHugh | |
| 5,310,759 A | 5/1994 | Bockman | |
| 5,324,746 A | 6/1994 | McKee et al. | |
| 5,510,384 A * | 4/1996 | McKee et al. ............... 514/530 | |
| 5,994,399 A | 11/1999 | McKee et al. | |

FOREIGN PATENT DOCUMENTS

WO   WO 91 16895   11/1991

WO   WO 92 21350   12/1992

OTHER PUBLICATIONS

The Merck Index, Thirteenth Edition, 2001-2005.*
Lie et al J. Periodontal. 1998, 69, 819-827.*
Eickholz et ak J. Clin. Periodontol. Feb. 2002, 29, 108-117.*
Yang, Chinese Dental Journal, vol. 8, No. 2, 1989, pp. 44-57.
Miller et al., BONE, vol. 14, No. 2, 1993, pp. 143-151.
Chao, Acta Anat., vol. 132, No. 4, 1988, pp. 304-309.
Levi et al., The Lancet, vol. 336, 1990, POG106, pp. 840-843.
Northway et al., CANCER, vol. 62, No. 9, 1988, pp. 1962-1969.
Lanas et al., J. Clin. Gastroenterol., vol. 13, No. 6, 1991, pp. 622-627.
Garris et al., Clin. Pharm., vol. 8, No. 9, 1989, pp. 627-644.
Rocha et al. Crit. Rev. Immunology, vol. 12, No. 3-4, 1992, pp. 81-100.
Lanza, Scand J. Gastroenterol., vol. 24, No. Suppl. 163, 1989, pp. 36-43.
Chem. Abstracts No. 164424, issued Nov. 5, 1984.
Biol. Abstracts No. 1101, issued Jul. 1, 1989.
"Periodontal Regeneration", Academy Report, American Academy of Periodontology, J. Periodontal, 2005:1601-1622.
Hellden et al., "The Effect Of Tetracycline And/Or Scaling On Human Periodontal Disease", Journal of Clinical Periodontology: 1979: 6: 222-230.
Bonito et al., "Impact Of Local Adjuncts To Scaling And Root Planing In Periodontal Disease Therapy: A Systematic Review," J. Periodontal, vol. 76, No. 8, 1227-1236, Aug. 2005.
Drisko, "Nonsurgical Periodontal Therapy," Periodontology 2000, vol. 25, 2001, 77-88.
Hanes et al., "Local Anti-Infective Therapy : Pharmacological Agents. A Systematic Review," Ann. Peridontol., vol. 8, No. 1, 79-98, Dec. 2003.
Hill et al., "Four Types Of Periodontal Treatment Compared Over Two Years," J. Periodontol, vol. 52, No. 11, 655-662, Nov. 1981.
Preshaw et al., "Subantimicrobial Dose Doxycycline As Adjunctive Treatment For Periodontitis," J. Clin. Periodontol 2004 ; 31: 697-707.
Ramfjord et al, "Results Following Three Modalities Of Periodontal Therapy," J. Periodontol, vol. 46, No. 9, pp. 522-526, Sep. 1975.

* cited by examiner

*Primary Examiner*—Shaojia Anna Jiang
*Assistant Examiner*—Ganapathy Krishnan
(74) *Attorney, Agent, or Firm*—Donald J. Pochopien

(57) ABSTRACT

The present invention is directed to a pharmaceutical composition comprising a therapeutically effective amount of misoprostol and an effective amount of an antibiotic. A suitable antibiotic is selected from the group consisting of doxycycline, gentamicin, tobramicin, ciprofloxacin, clindamycin, clarithromycin, azithromycin and metronidazole. Preferred antibiotics are doxycycline and ciprofloxacin. More preferably, the antibiotic is doxycycline. In its second aspect, the present invention is directed to a method for treating periodontal disease in a mammalian patient comprising administering to a mammalian patient in need of such treatment a therapeutically effective amount of misoprostol and an effective amount of an antibiotic. Typically, the mammalian patient is a human.

23 Claims, 4 Drawing Sheets

METHOD AND COMPOSITION FOR TREATING PERIODONTAL DISEASE

FIELD OF THE INVENTION

The present invention is directed to pharmaceutical compositions and a method for using such compositions to regenerate bone and tissue in dental pockets

BACKGROUND OF THE INVENTION

Periodontitis is a chronic inflammatory response caused by bacterial plaque that has spread below the gum line. Starting in the early stages as gingivitis, the later stages of periodontitis involves inflammation of the gums, connective tissues, and bones surrounding the teeth i.e. alveolar bones. Prolonged inflammation causes degenerative loss of tissues supporting the teeth and alveolar bone loss, eventually leading to loss of teeth. Tooth loss, caused by the loss of alveolar bone, is one of the major problems in clinical dentistry. In fact, periodontitis is the primary cause of tooth loss. It is approximated that 140 million adults, in the United States alone, exhibit various stages of periodontal disease.

The periodontitis-associated inflammation occurring in the surrounding tissues that support the teeth is characterized by formation of infected "pockets" or spaces between the teeth and gums. These infected pockets contain debris, predominantly composed of microorganisms and their products (enzymes, endotoxins and other metabolic products), dental plaque, gingival fluid, food remnants, salivary mucin, desquamated epithelial cells, and leukocytes. Periodontal pockets are chronic inflammatory lesions, and as such are constantly undergoing repair. The condition of the soft tissue walls of the periodontal pocket results from a balance between destructive and constructive tissue changes. The destructive changes consist of the fluid and cellular inflammatory exudates and the associated degenerative changes stimulated by local bacterial infiltrate. The constructive changes consist of the formation of connective tissue cells, collagen fibers, and blood vessels in an effort to repair tissue damage caused by the inflammatory process. Healing does not go to completion because of the persistence of local irritants i.e., bacteria and the enzymes that they produce. These irritants stimulate fluid and cellular exudates, which in turn causes degeneration of the new tissue elements formed in the repair process. If purulent exudates are present in the infected pockets, it can contain living, degenerated and necrotic leukocytes (predominantly polymorphonuclear), living cells and dead bacterial cells, serum and a small amount of fibrin.

The most basic treatment for periodontitis is scaling and root planing procedures. These procedures involve manually removing calculus, plaque and other deposits, smoothing the root surface to rid it of necrotic tooth substances, and curetting the inner surface of the gingival wall of the periodontal pockets to separate away any diseased soft tissue. The procedures aim to eliminate the infected pockets by reattaching connective tissue and epithelium to the tooth surface. By eliminating the environment for the microorganisms to grow, scaling and root planing procedures can successfully obliterate the infected pockets. These procedures may result in the replacement of diseased soft tissue with new soft tissue from growth and differentiation of new cells and intercellular substances. However, scaling and root planing procedures are ineffective in stimulating re-growth or replacement of destroyed bone and cementum caused by severe periodontitis. Hence, there is a need for reliable or predictable methods to regenerate, augment, or restore alveolar bone loss and cementum loss inflicted by periodontitis.

Another initial treatment for periodontitis is administration of antibiotics, which may be optionally performed in conjunction with scaling and root planing procedures. Tetracycline is the most commonly administered antibiotic for periodontitis; however, numerous other types of antibiotics can also be employed because human periodontal pockets harbor highly diverse populations of bacteria. In fact, a recent study by Paster et al. (Paster, B. J., *Journal of Bacteriology*, Vol. 183 (12), p. 3770-3790, 2001) recorded 91 different bacterial species or phylotypes from cultures collected from periodontal diseased sites in human patients. In those patients who suffered from refractory periodontitis, collected cultures revealed the presence of 213 different bacterial species or phylotypes present. Novel bacterial species or phylotypes, in addition to known putative periodontal pathogens such as *Porphyromonas gingivalis, Bacteroides forsythus*, and *Treponema denticola*, were observed in these cultures. In addition to tetracycline, other antibiotics, such as minocycline, as described in U.S. Pat. No. 4,701,320 (the entire disclosure of which is incorporated herein by reference), and amoxicillin and metronidazole, as described in U.S. Pat. No. 4,997,830 (the entire disclosure of which is incorporated herein by reference), have been employed for the treatment of periodontitis. Despite the effectiveness of antibiotics in reducing inflammation and bacterial infection, antibiotic administration, like scaling and root planing, is also deficient in stimulating re-growth or replacement of the destroyed bone and cementum caused by severe periodontitis.

A more dramatic therapy for patients who are not responsive to scaling and root planing procedures and/or antibiotic administration is periodontal surgery, such as gingivectomy or periodontal flap surgery. In gingivectomy, the dentist reshapes the unhealthy gum tissue in order to reduce the size of the infected pocket. Reduction of the pocket size allows the patient to hygienically maintain the pocket by routine brushing and flossing, thereby eliminating a favorable environment for bacterial growth. Periodontal flap surgery is performed also when scaling and root planing procedures are unsuccessful, especially when there is loss of bone or tissue detachment. In this procedure, incisions are made in the gums and the surrounding alveolar bone is re-contoured to assist in healing of the infected area. Since only one quadrant of the mouth can be operated on at a time, multiple visits to the dentist are required and the entire surgical procedure can extend over a period of a month or longer. In addition to the invasive nature and the inherent pain involved with surgery, both procedures of gingivectomy and periodontal flap surgery are insufficient in stimulating re-growth or replacement of the destroyed bone and cementum caused by severe periodontitis.

In an effort to address the problem of alveolar bone loss caused by periodontitis, therapeutic compositions containing substances that specifically stimulate osteogenesis in mammalian skeleton have been developed. One such substance is prostaglandin E1 ($PGE_1$). In vitro studies, as described for example in Flanagan et al. (Flanagan, A. M. et al., *Endocrinology*, Vol. 130 (1), p. 443-448, 1992), have shown that culturing mammalian calvarial cells in the presence of $PGE_1$ increases the formation of mineralized nodules. Formation of these nodules is advantageous because they give rise to osteoprogenitor cells, which are responsible for mediating the process of bone anabolism (Miller et al., *Clinics in Plastic Surgery*, Vol. 21 (3), p. 393-400, July 1994). The role of $PGE_1$ in bone formation has been confirmed by in vivo studies performed on adult dog models. A study by Marks et al. (Marks, S. C. et al., *J. Oral Pathol.*, Vol 17, p. 500-505, 1988) shows that local application of $PGE_1$ can stimulate new bone formation adjacent to sites of delivery in the canine mandible long bone and that local delivery of $PGE_1$ increases the thickness and appositional rate of alveolar bone in the canine mandible. A further study, also by Marks et al. (Marks, S. C. et al., *J. Periodont. Res.*, Vol. 29, p. 103-108, 1994) shows that local delivery of $PGE_1$ to the canine mandible increases alveolar bone height and regenerates cementum and periodontal ligaments around the premolars and molars of adult dogs. These in vivo studies demonstrate that $PGE_1$ can promote osteogenesis and increase bone mass.

Recently, topical compositions comprising a synthetic and more stable $PGE_1$ analog, called misoprostol, have been developed as conjunctive therapy with scaling and root planing procedures. As described, for example in U.S. Pat. Nos. 5,324,746 and 5,510,384 (the disclosures of which are incorporated herein by reference), these compositions are effective in treating periodontal disease and can also be used to treat damaged tissue caused by, for example, chemotherapy or radiotherapy. Other applications for compositions comprising misoprostol include regeneration of collagen-containing human tissue, such as skin, bone, connective tissue, and cartilage, as described for example in U.S. Pat. No. 5,994,399 (the disclosure of which is incorporated herein by reference).

An object of the present invention is to provide a pharmaceutical composition and methods that are more effective than misoprostol alone or current methods in regenerating bone and cementum in periodontal pockets of patients afflicted with periodontal disease.

BRIEF SUMMARY OF THE INVENTION

The Applicants unexpectedly discovered a method for obtaining exceptional results in treating mammalian patients afflicted with periodontal disease, particularly in obtaining very significant regeneration of bone and cementum in periodontal pockets as determined by the very significant reduction in the depth of the periodontal pockets with or without surgical intervention (i.e., scaling, root planing and curettage). More specifically, the Applicants discovered that treating a mammalian patient afflicted with periodontal disease with a combination of an antibiotic that is effective against one or more plaque causing bacterium that are found in a periodontal pocket (hereinafter an "antibiotic") and with misoprostol produced an unexpectedly superior reduction in the depth of the periodontal pockets in the afflicted patients. At the 6-week observation, the patients receiving the dual regimen, comprising systemically administering a standard dosing regimen of systemic antibiotic over the prescribed dosing period (typically 10 days) followed by topically applying misoprostol to the dental pocket(s), performed as well as the patients treated with the single dosing regimen of antibiotic only. However, at the 52-week observation, the patients receiving the dual regimen showed the greatest reduction in pocket depth of all groups. The dual drug treatment regimen was the only treatment that resulted in a trend towards apparent continued improvement in pocket depth between the Week 6 and the Week 52 observations. These patients had approximately 40-50% mean reductions in pocket depth at Week 6, and approximately 50-60% percent mean reduction at Week 52.

The most unexpectedly superior reduction in pocket depth was obtained after only three weeks of treatment when the patients afflicted with periodontal disease were pretreated systemically with a standard dosing regimen of an antibiotic for 10 days followed by topically applying for three weeks to, at, on, onto, in, into or near the periodontal pockets a pharmaceutical composition comprising an effective amount of misoprostol and an effective amount of an antibiotic.

Thus, the present invention has multiple aspects. In one aspect, the present invention is directed to a pharmaceutical composition comprising in combination a therapeutically effective amount of misoprostol and an effective amount of an antibiotic. A suitable antibiotic is selected from the group consisting of tetracycline, doxycycline, gentamicin, tobramicin, ciprofloxacin, clindamycin, clarithromycin, azithromycin and metronidazole. Preferred antibiotics are doxycycline and ciprofloxacin. More preferably, the antibiotic is doxycycline. The pharmaceutical composition typically utilizes one or more pharmaceutically acceptable carriers for topical application in the mouth (also referred to herein as "oral" application), and preferably, is applied in paste form, more preferably utilizing a dental adhesive.

In its second aspect, the present invention is directed to a method for treating periodontal disease in a mammalian patient comprising administering to a mammalian patient in need of such treatment a therapeutically effective amount of misoprostol and an effective amount of an antibiotic. Typically, the mammalian patient is a human. However, the term "mammalian patient" as used herein is intended to cover other mammals than humans. Such other mammals include mammals treated by veterinarians. Preferred other mammals include domesticated animals, such as dogs, cats, horses, cattle, sheep, goats, pigs and primates.

In one embodiment of the inventive method, the antibiotic is administered to the mammalian patient separately from the misoprostol. In this embodiment, the antibiotic is administered systemically to the patient whereas the misoprostol is topically applied to, at, on, onto, in, into or near the periodontal pocket. This topical administration is also known in the art as "local" administration.

In another embodiment of the inventive method, the effective amount of misoprostol is topically applied in a pharmaceutical composition that also contains a topically effective amount of antibiotic. Preferably, the pharmaceutical composition that is used for the topical administration contains one or more pharmaceutically acceptable carriers that are sufficiently adhesive so as to retain the composition as a whole at, on, onto, in, into or near the periodontal pocket. Suitable carriers are known in the art and more fully discussed herein. It is also within the scope of this latter embodiment that the patient be systemically pre-treated (i.e., treated prior to administration of the misoprostol) with a typical dosing regimen of antibiotic. As reflected in the Physician's Desk Reference (PDR), a typical systemic dosing regimen for most antibiotics is oral administration over a period of 10 days.

The present method for treating periodontal disease optionally includes the step of administrating sub-gingival scaling, root planing, or curettage in the afflicted patient. This step is optionally administered prior to, during or immediately after systemically pretreating the mammalian patient with an effective amount of antibiotic. Preferably, this step is administered prior to systemically treating the mammalian patient with an effective amount of antibiotic.

In a particularly preferred embodiment, the present invention is directed to a method for treating periodontal disease in a mammalian patient comprising (a) administering to, at, on, onto, in, into, or near a periodontal pocket of the patient in need of treatment a pharmaceutical composition comprising a therapeutically effective amount of misoprostol or a pharmaceutically acceptable derivative or salt thereof in a pharmaceutically acceptable carrier; (b) administering to, at, on, onto, in, into, or near a periodontal pocket of said patient in need of treatment a pharmaceutical composition comprising an antibiotic that is effective against bacteria suspected of causing bacterial plaque in a pharmaceutically acceptable carrier; and (c) optionally, prior to step (a) or step (b), performing sub-gingival scaling, root planing, or curettage in said patient. Preferably, steps (a) and (b) are performed simultaneously, more preferably, simultaneously in a single pharmaceutical composition containing both the misoprostol and antibiotic.

DETAILED DESCRIPTION OF THE INVENTION

Figure 1A:
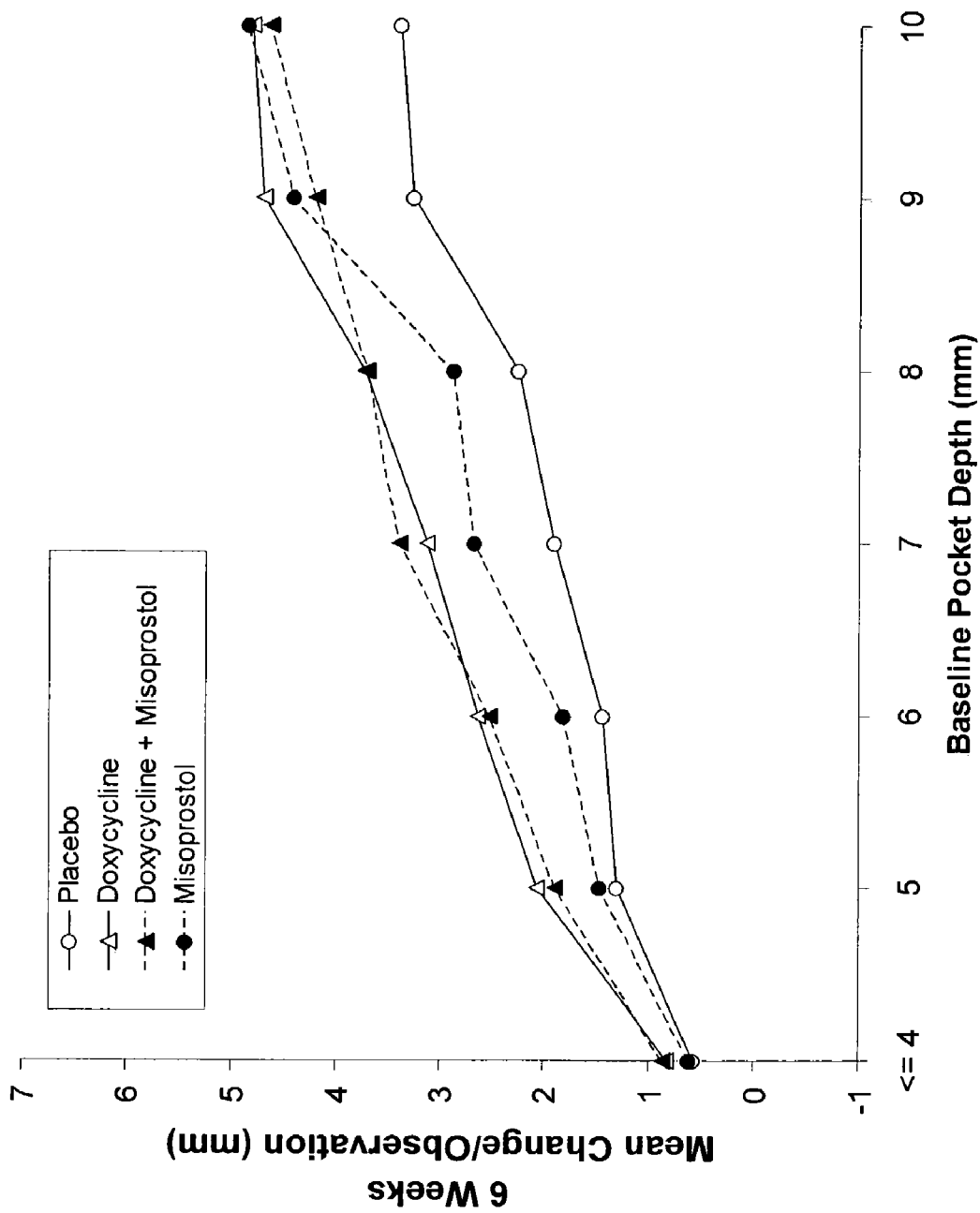
FIG. 1A is a comparative graph of the mean change in pocket depth (mm) per observation versus the baseline pocket depth (mm) at 6 weeks post-treatment for the following four treatment modalities: placebo (open circle); doxycycline (open triangle); doxycycline+misoprostol (shaded triangle); and misoprostol (shaded circle) for N=58.

The present invention has multiple aspects. In its first aspect, the applicants have discovered a superior treatment for periodontal disease is achieved by a pharmaceutical composition comprising a therapeutically effective amount of misoprostol and a therapeutically effective amount of an antibiotic in a pharmaceutically acceptable carrier.

The first active ingredient, misoprostol, is an analog of $PGE_1$ in which the carbon 15 (C-15) hydroxyl group has been removed and replaced by a hydrogen atom, and the two hydrogen atoms at the carbon-16 (C-16) position have been removed and replaced by a methyl group and a hydroxyl group. By adding a methyl group to the C-16 position, the C-16 hydroxy group becomes less susceptible to the action of 15-dehydrogenase enzymes that inactivate natural prostaglandins. In addition, the C-16 position of the hydroxyl group, rather than the 15-position as in natural $PGE_1$, reduces side effects, such as diarrhea, compared with the natural $PGE_1$.

Misoprostol, methyl-(11α, 13E)-11,16-dihydroxy-16-methyl-9-oxoprost-13-en-1-oate, is racemic, existing as four stereoisomers in the 16R(±)- or 16S(±)-stereoisomeric forms. Misoprostol is commercially available from the G. D. Searle Division of Monsanto under the trade name CYTOTEC® as a double racemate of two diastereomers containing four stereoisomers. Structurally, these stereoisomers are characterized by the structures shown below:

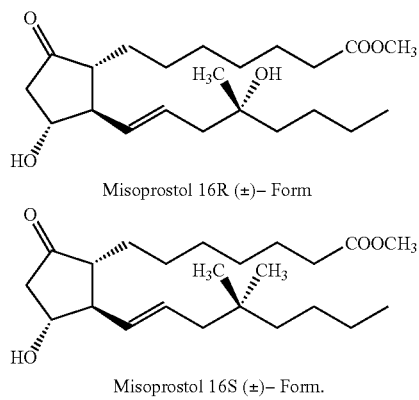

Misoprostol 16R (±)– Form

Misoprostol 16S (±)– Form.

Misoprostol binds to both $PGE_1$ and $PGE_2$ receptors, although only one of its four stereoisomers is thought to be responsible for mediating receptor activity. It is unknown as to which of the four stereoisomers is the active agent. Thus, it is reasonable to expect that some effect, such as those derived from misoprostol competing with $PGE_1$ at its binding site, for instance, will show significant stereospecificity. When administered, misoprostol is rapidly de-esterified to its active form, misoprostolic acid. Misoprostolic acid is approximately 85% albumin bound and has a half-life of about 30 minutes, mostly being excreted in urine as inactive metabolites.

In addition to being used in topical compositions for the treatment of periodontitis, as described, for example, in U.S. Pat. Nos. 5,324,746 (the entire disclosure of which is incorporated herein by reference), misoprostol has been used in the past on a prescription basis as a gastric mucosa protectant and antiulcer agent. Misoprostol induces marked edema of the mucosa and submucosa (increasing the thickness of both layers), dilating interglandular regions of the lamina propria, reducing depth and width of gastric foveolae, vasodilating vascular channels, reducing the height of surface epithelial cells, swelling basolateral intercellular spaces, and increasing the amount of adherent mucosa. The mucosal edema and increased mucus layer may be important component in misoprostol's cytoprotective mechanism (Davies, N. M. et al., *Pharmacotherapy*, Vol. 21(1), p. 60-73, 2001). The primary use for misoprostol is the prevention of nonsteroidal anti-inflammatory drug-induced (NSAID) gastric ulcers, and short term treatment of duodenal ulcers. Additional diseases for which misoprostol is being developed as a viable therapeutic agent include, for instance, NSAID-induced small bowel damage, dysfunctional pancreatic enzyme function and imbalanced duodenal pH caused by cystic fibrosis, and hepatic and pancreatic tissue injury and related GI damage (Shield, M. J. et al., *Pharmac. Ther.*, Vol. 65, p. 125-147, 1995).

In its second aspect, the present invention is directed to a method for treating periodontal disease comprising administering to a patient in need of treatment a pharmaceutical composition comprising a therapeutically effective amount of misoprostol or a pharmaceutically acceptable derivative or salt thereof, and an effective amount of an antibiotic. As used herein, the term "therapeutically effective amount of misoprostol" is typically from about 1 microgram (μg) to about 40 micrograms, preferably from about 5 micrograms to about 30 micrograms, more preferably from about 10 micrograms to about 20 micrograms, and most preferably from about 10 micrograms to about 12 micrograms. According to the invention, misoprostol or pharmaceutically acceptable derivatives or salts thereof can be in the form of any pharmaceutically active racemate, enantiomer, or diastereomer. In addition, any pharmaceutically acceptable misoprostol derivative, such as misoprostolic acid, can be used in the method or compositions of the invention.

Antibiotics that may be used in the compositions and method of the invention include, but are not limited to, antibiotics selected from the group consisting of tetracycline derivatives, preferably doxycycline; an aminoglycoside, such as gentamicin or tobramicin; a fluoroquinoline derivative, such as ciprofloxacin; a lincomycin derivative, such as clindamycin; a macrolide derivative, such as clarithromycin; an azalide derivative, such as azithromycin; and an imidazole derivative, such as metronidazole. By the term "a therapeutically effective amount of an antibiotic" is meant, for a given antibiotic, an amount of an antibiotic that effectuates stasis or a reduction in the overall bacterial population in a periodontal pocket. In one embodiment of the present invention, the antibiotic was administered systemically so as to achieve a therapeutically effective amount of antibiotic in the blood and ultimately at the periodontal pocket. In a formulation that provides unexpectedly superior results and that facilitates patient compliance, a therapeutically effective amount of antibiotic was administered topically to, at, in, onto, into or near the periodontal pocket with a therapeutically effective amount of misoprostol. Preferably, the antibiotic and the misoprostol for topical application are contained within the same pharmaceutical composition.

In embodiments comprising systemically administered doxycycline, a therapeutically effective amount is know to the art and typically ranges from about 20-100 mg twice daily (BID) for one day (a loading dose) and from about 50-200 mg once each day (QD) for nine days, more typically from about 50-100 mg twice daily (BID) for one day and from about 50-100 mg once daily (QD) for nine days, and most typically about 100 mg twice daily (BID) for one day and about 100 mg once daily (QD) for nine days. For the topically administered doxycycline, a therapeutically effective amount comprises from 0.1 to 3 cc (ml) of a pharmaceutical composition having from 0.1-5% of doxycycline, typically, about 0.1 to 3 cc of a pharmaceutical composition having about 1% doxycycline. Similar formulations are made for tetracycline and minocycline.

In embodiments comprising systemically administered gentamicin or tobramicin, for example, a therapeutically effective amount of the antibiotic is known in the art. For the topically administered gentamicin, a therapeutically effective amount comprises from 0.1 to 2 cc (ml) of a pharmaceutical composition having from 0.1-5% of gentamicin, typically, about 0.1 to 2 cc of a pharmaceutical composition having from 0.1-1% of gentamicin, more typically, about 0.1 to 2 cc of a pharmaceutical composition having about 0.1% gentamicin.

In embodiments comprising systemically administered ciprofloxacin, for example, a therapeutically effective amount is known in the art and typically ranges from about 250-700 mg twice daily (BID) for five to ten days, more typically for ten days. For the topically administered ciprofloxacin, a therapeutically effective amount comprises from 0.1 to 5 cc (ml) of a pharmaceutical composition having from 0.1-5% of ciprofloxacin, typically, about 0.1 to 5 cc of a pharmaceutical composition having from 0.1-1% of ciprofloxacin, more typically, from 0.1 to 5 ml of a pharmaceutical composition having about 1% ciprofloxacin.

In embodiments comprising systemically administered clindamycin, for example, a therapeutically effective amount is known in the art and typically ranges from about 37.5-300 mg every 6-8 hours (3-4 times daily) for 5-10 days, more typically from about 150-300 mg every 6 hours (QID) for 5-10 days. For the topically administered clindamycin, a therapeutically effective amount comprises from 0.1 to 3 cc (ml) of a pharmaceutical composition having from 0.1-5% of clindamycin, typically, about 0.1 to 3 cc of a pharmaceutical composition having about 1% clindamycin.

In embodiments comprising clarithromycin, for example, for example, a therapeutically effective amount is known in the art and typically ranges from about 125-1000 mg once to twice daily (BID) for ten days, more typically from about 250-500 mg twice daily (BID) for 10-14 days or 1000 mg once daily for 10-14 days. For the topically administered clarithromycin, a therapeutically effective amount comprises from 0.5 to 3 cc (ml) of a pharmaceutical composition having from 0.1-5% of clarithromycin, typically, about 0.5 to 3 cc of a pharmaceutical composition having about 2% clarithromycin.

In embodiments comprising azithromycin, for example, for example, a therapeutically effective amount is known in the art and typically ranges from about 50-500 mg once daily for one day (a loading dose) and about 250 mg once each day (QD) for four more days, more typically from about 500 mg once daily for one day and from about 250 mg once daily for four more day. For the topically administered azithromycin, a therapeutically effective amount comprises from 0.1 to 3 cc (ml) of a pharmaceutical composition having from 0.1-5% of azithromycin, typically, about 0.1 to 3 cc of a pharmaceutical composition having from 0.5-2% of azithromycin, more typically, about 0.1-3 cc of a pharmaceutical composition having about 1% azithromycin.

In embodiments comprising metronidazole, for example, for example, a therapeutically effective amount is known in the art and typically ranges from about 250-2000 mg twice (BID) to four (QID) times daily for five to ten days. For the topically administered metronidazole, a therapeutically effective amount comprises from 0.1 to 3 cc (ml) of a pharmaceutical composition having from 0.1-5% of metronidazole, typically, about 0.1 to 3 cc of a pharmaceutical composition having from 0.75-2% of metronidazole, more typically, about 0.1 to 3 cc of a pharmaceutical composition having about 0.75% metronidazole.

According to the invention, the present pharmaceutical compositions may comprise more than one antibiotic, such as a combination of antibiotics. Compositions comprising combinations of antibiotics for the treatment of periodontitis have been previously described. For example, U.S. Pat. No. 4,997,830 (the disclosure of which is incorporated herein by reference) describes an oral composition comprising metronidazole and amoxicillin for the treatment of periodontal disease.

Pharmaceutical compositions presented herein may be prepared in various formulations to produce a variety of final products that are useful for treating periodontal disease. For instance, for topical administration to periodontal pockets, formulations such as toothpaste, mouthwash, chewing gum, and other dentifrices are embodiments of the pharmaceutical composition of the invention. In addition, topical formulation products, such as gels, creams, lotions, ointments, and timed-release liposomes are also embodiments of the present invention. Topical and/or oral compositions of this invention can be formulated with an appropriate choice of one or more pharmaceutically acceptable carriers. Pharmaceutically acceptable carriers suitable for use with this invention include, for example, vegetable or mineral oils, white petrolatum or white soft paraffin, branched chain fats or oils, animal fats, and alcohols, such as absolute ethanol. Acceptable carriers may also be in soluble form. Emulsifiers, stabilizers and anti-oxidants may also be included as well as agents imparting color or fragrance if desired.

The pharmaceutical compositions of the present invention for topical (local) application may further comprise colloidal dispersion systems, such as carbowax; additives or preservatives, such as polyethylene glycol having an average molecular weight ranging, for example, from about 300 MW to about 1450 MW; denture adhesives, such as SUPER WERNET'S® Denture Adhesive Powder (90% hypromellose, USP (2-hydroxypropyl methylcellulose) 10% polyox WSR-301 (polyethylene oxide water soluble resin, MW approximately 4,000,000)); and/or a solvent, such as absolute ethanol or aqueous sodium chloride.

Oral pastes containing the present pharmaceutical compositions may be formulated by any method known. In an embodiment, 2.3 mg misoprostol (i.e., pulverized 11.5×200 microgram tablets of CYTOTEC®) was combined with 15 grams of SUPER WERNET'S® Denture Adhesive Powder, 0.86 grams of polyethylene glycol (1450 MW), and 16.34 grams of polyethyleneglycol (300 MW). Use of the denture powder has been shown to allow a slower release of the active agents from the application site on the oral mucosa. The oral paste (71 µg misoprostol/ml) delivers a dose of 10 micrograms of misoprostol per application dose of 140 mg (0.12 ml) and can be dispensed in two 10 ml syringes. The oral paste can be applied over the area where the gingival tissue meets the tooth lingual, palatal and buccal surfaces.

Oral washes containing the present pharmaceutical compositions may be formulated by any method known. In an embodiment, 0.06 ml of a solution of misoprostol in absolute ethanol (400 micrograms of misoprostol per ml) is diluted to 1.0 ml with 0.9% sodium chloride. The oral wash may be used for flushing infected pockets.

Creams can be formulated from a mixture of mineral oil, self-emulsifying beeswax and water in which mixture the active ingredient, dissolved in a small amount of an oil such as almond oil, is admixed. A typical example of such a cream is one which includes about 40 parts water, 20 parts beeswax, 39 parts mineral oil and about 1 part almond oil.

Ointments may be formulated by mixing a solution of the active ingredient(s) in a vegetable oil such as almond oil with warm soft paraffin and allowing the mixture to cool. A typical example of such an ointment is one which includes about 30% almond oil, and about 70% white soft paraffin by weight.

Lotions may be conveniently prepared by dissolving the active ingredient, in a suitable high molecular weight alcohol, such as propylene glycol or polyethylene glycol, having a molecular weight of about 300 to about 1450 MW.

It should be recognized that misoprostol will break down to prostaglandin A if in the presence of water. Thus, creams last approximately only one week because of this stability problem. Therefore, misoprostol is best used in a powder form that can be hydrated at the time of use. Misoprostol is more stable in a vehicle that uses propylene glycol. It can be stored in a dry state for a couple years if it is stabilized with hydroxypropyl methyl cellulose. In liquid form as the oil, it is preferably dissolved in absolute alcohol (ethanol) and frozen. The frozen alcohol and misoprostol mixture is stable for at least a year.

In addition, plasticizers, additives, colorants, preservants, and protectants may be added to the present pharmaceutical compositions to enhance aesthetic and mechanical features (i.e. softness and flexibility). The type and amount of plasticizer, additive, colorant, preservant, and/or protectant to be used can be readily optimized to achieve a desired effect. Also, surfactants and drying agents may be added as well to the pharmaceutical composition to achieve a desired effect. Non-limiting examples of surfactants include stearoyl lactylate, calcium steroyl lactylate, and glyceryl monosterarate. Non-limiting examples of drying agents include magnesium aluminum silicate and sodium, magnesium and potassium sulfate, and hydrophilic clays. The present pharmaceutical compositions may also contain taste modifiers, coloring agents, and moisture retaining agent. Examples of taste modifiers include non-reducing sugars, such as xylitol, malitol, or Lycasin® manufactured by Roquette America Inc. of Keokuk, Iowa. Examples of moisture retaining agents include celluloses, cellulose derivatives, starches, starch derivatives, vegetable gums, non-hygroscopic mono- and di-oligosaccharides, and silicon dioxide.

One or more additional substances which have therapeutic effects on the skin and/or tissue being treated may also be incorporated in the composition. For example, other suitable types of active ingredients may be incorporated in the compositions of this invention and may include other compounds known to have beneficial effect on skin and/or collagen-containing tissue. Additionally, the pharmaceutical composition of the present invention may optionally include an anti-inflammatory agents and/or a local anesthetic, such as dyclonine in an amount of about 0.5 to 1% by weight.

Dosage formulations of the present pharmaceutical compositions can be prepared by combining them with a pharmaceutically acceptable carrier, such as a slow release agent, to make either immediate or slow release formulations as is well known in the art. Such pharmaceutically acceptable carriers may be either solid or liquid in form such as, for example, cornstarch, lactose, sucrose, peanut oil, olive oil, sesame oil, propylene glycol and water. If a solid carrier is used, the dosage formulation of the present pharmaceutical compositions may be in, for example, powder, troche, or lozenges form. If a liquid carrier is used, the dosage formulation of the present pharmaceutical compositions may be in, for example, soft gelatin capsule, syrup liquid suspension, emulsion, or solution form. The dosage formulations may also contain adjuvants, such as preserving, stabilizing, wetting or emulsifying agents, or solution promoters. Immediate and slow release formulations are well known in the art and have been described, for example, in U.S. Pat. No. 4,764,377 (the disclosure of which is incorporated herein by reference), which describes a method for treating periodontal disease by means of a delivery device placed within the periodontal pocket so that release of an antibiotic, such as tetracycline, occurs in the immediate vicinity of the disease process.

In the method of the present invention, the pharmaceutical compositions are administered to a patient one or more times daily. For example, the present pharmaceutical composition is typically administered from about one time to about six times daily, more typically about two times to about five times daily, and most typically about three times to about four times daily.

As presented herein, methods of the instant invention for treating periodontal disease can optionally further comprise administering to a patient at least one step of sub-gingival scaling, root planning, or curettage. These procedures involve-manually removing calculus, plaque and other deposits, smoothing the root surface to rid of necrotic tooth substances, and curetting the inner surface of the gingival wall of the periodontal pockets to separate away the diseased soft tissue.

In the method of the present invention, administering a pharmaceutical composition containing misoprostol, in combination with an antibiotic, was found to be unexpectedly superior to administering either misoprostol or antibiotic alone, or the sum of their individual contributions. Amelioration of periodontal disease by the present pharmaceutical compositions is indicated by at least one of the following characteristics: regeneration of tooth-supporting tissues, improvement of periodontal-involved teeth, regeneration of infra bony defects, regeneration of alveolar bone or tissue, reduction of pocket depths, decrease in tooth mobility, reduction in soft tissue inflammation or edema, or reduction in bacterial colonization or infection. Topical application of misoprostol with doxycycline, for example, resulted in statistically significant improvements in pocket depth when compared to treatment with doxycycline or misoprostol alone, or the sum of their individual contributions. The results of this study indicate that topical administration of misoprostol, with and without pre-treatment with doxycycline, results in significant improvements in periodontal disease compared to the current standard of care, doxycycline and/or sub-gingival planing, scaling and curettage. Although there were no statistically significant differences between the three active treatments at six weeks post-treatment, at 52 weeks post-treatment, administration of doxycycline+misoprostol and placebo+misoprostol resulted in statistically significantly greater improvements in mean pocket depths compared to doxycycline+placebo. In fact, most patients in the doxycycline+placebo group showed regression of the disease at 52 weeks post-treatment, where changes in pocket depths in the doxycycline+placebo group were statistically indistinguishable from those in the placebo group. See FIGS. 1-4.

Effect of Scaling, Root Planing and Curettage The scaling, root planning, and curettage procedure, even without additional treatment, benefits the patient by providing an approximately 25-30% reduction in pocket depth as long as one year later. However, there is a continuing search to find methods of increasing the level of benefit, and prolonging the period of effectiveness.

Effect of Doxycycline Doxycycline is a tetracycline antibiotic with activity against anaerobic bacteria. A 10-day pre-treatment program is intended to significantly reduce the bacterial colonization in the interface between the soft tissue and hard tissue structures. A full 10-day period may not be necessary to have produced just this effect, but the additional time also allows the infection-induced inflammation and edema in the soft tissues to subside and be considerably reduced. The subsequent scaling and root planing then removes most or all of the calculus and biofilm that promote the bacterial colonization.

Doxycycline treatment, or any other antibiotic treatment by itself, is unlikely to be consistently successful in a large proportion of the patients with moderate or severe periodontal disease of the type treated in this study. First, removal of the calculus and destruction of the biofilm along with removal of chronic tissue that lines the diseased pocket are critical for the elimination of sites that serve as bioreservoirs for reinfection and which promote recolonization. Second, the effectiveness of all commercially available antibiotics can be circumvented by the emergence of resistant strains. Low antibiotic concentrations and long-term, chronic treatment are well known to serve as environmental pressures that can lead to the emergence of resistant strains. The emergence of a resistant strain will very probably be characterized by a recurrence of the infection, inflammation, edema and tissue sensitivity that characterized the original disease. Third, while this study employed oral doxycycline as the antibacterial medication, there are other commercially available products that directly target the gingival tissue by slow release of antibiotic from string, wafer, or gel embedded in the pocket between the soft and hard tissues. These products have the disadvantage of physically separating the two tissues, thus inhibiting the attachment of the two structures, and ultimately, closure of the pocket.

As expected with any antibiotic, halting the administration of the drug, without controlling the sources of reinfection, ultimately leads to a resurgence of the disease state, and a return to the previous state of infection or even further progression of the disease. Patients randomized to the doxycycline pre-treatment program alone showed this pattern of response. While there was an early positive response that was at least as good as any of the other options, the initial benefit dissipated completely within one year so that at the end of that year the treatment program was indistinguishable from a placebo treatment with scaling and root planing, no matter how deep or shallow the original pocket depth.

Effect of Misoprostol Misoprostol is a prostaglandin E1 analog that has been implicated in the stimulation of bone growth and remodeling and in the proliferation of connective and epithelial tissues. (Marks, S. C. Jr., Miller, S. C. Local infusion of prostaglandin E-1 stimulates mandibular bone formation in vivo. J. Oral Pathol 1988, 17: 500-505; Marks, S. C. Jr., Miller, S. C. Site-directed formation of new lamellar bone in adult dogs by infusion of prostaglandin E-1, Dixon, A. D., Samat, B. G., Hoyte, D. A. N., eds. Fundamentals of bone growth: Methodology and applications. Boca Raton, Fla.: CRC Press: 1991: 375-381; Marks, S. C. Jr., Larson, E. K., Bowman, B. M., Miller, S. C. Local induction of alveolar bone in adult dogs by infusion of prostaglandin E-1, Davidovitch, Z, ed., Biological mechanisms of tooth movement and craniofacial adaptation. Columbus, Ohio: Ohio State University Press: 1992, 137-142; Marks, S. C. Jr., Miller, S. C. Local delivery of prostaglandin E-1 induces periodontal regeneration in adult dogs. J. Periodont Res. 1994, 29: 103-108; and Flanagan, A. M., Chambers, T. J. Stimulation of bone nodule formation in vitro by prostaglandin E-1 and E-2. Endocronology 1992, 130: 433.) Misoprostol's role as a commercial product (CYTOTEC®) as a cytoprotective agent may be due, at least in part, to this stimulatory proliferative effect on epithelial cells in the gut. Local administration of misoprostol as part of these dental procedures was suggested by results published by others that showed prolonged, low dose administration of prostaglandins stimulated growth of alveolar bone, connective tissue fibers for reattachment and new cementum. The new alveolar bone was laid down without previous bone resorption.

Local application of the misoprostol-containing gel by the patients in this study enhanced the beneficial effect of scaling, root planning and curettage in the short-term, and added to and prolonged the enhanced benefits provided by doxycycline pre-treatment. Since misoprostol's postulated mechanism of action in this setting, promoting bone growth is not a rapid process and takes substantial time to show its cumulative effect, it is not surprising that significant added benefit was not seen by the Week 6 observation. However, the benefit continued to accrue beyond that time point, even though the administration of misoprostol was no longer continuing.

This continued accrual of effect is not necessarily an indication of a "prolonged duration of action" for misoprostol, but is probably just the result of misoprostol stimulating the development of some vital, but unmeasured, tissue infrastructure. For instance, it is possible that the 6 weeks of misoprostol application stimulated the formation of a bone lattice structure in the region cleaned of calculus, biofilm and chronic tissue by the scaling, root planning and curettage. This would not be substantial enough at 6 weeks to resist probing, but would be sufficient to promote the activity of osteoblasts over: the intervening several months. Freeing the surfaces and tissue of bacterial colonization by the doxycycline pre-treatment would make this process even more likely to succeed, and promote the involvement of more surface area. Consistent with this hypothesis is the observations of the principal investigator at the quarterly return visits that patients within the treatment groups ultimately identified as receiving misoprostol, showed improvements in tooth mobility, whereas patients in the other groups did not. This would be in spite of the fact that pocket depths and improvements in pocket depth were apparent in all cases. Improvements in pocket depth requires only the close adhesion of the epithelial cells to the hard tissues, whereas decreased tooth mobility requires laying done of additional bone matrix.

Radiographs should be able to be used to document the formation of new bone within the previously diseased areas. Unfortunately in this study, the attempt to provide this information was hindered by the unexpected deterioration of the impression materials that were used to construct the step-wedges to index the "before" and "after" radiographs. While it is possible to detect apparent increases in bone tissue near the roots of the teeth, the quantitative interpretation is open to the criticism that the results might be biased by alterations in the angle of viewing.

Another conclusion provided by these results is that more severe periodontal disease of this type may be able to be treated by successive rounds of scaling, root planning and curettage with doxycycline pre-treatment and misoprostol post-treatment. It might well be possible to completely fill in even very large pockets if one successively repeats the treatment program, tailors the treatment repeat schedule over a period of time that allows the bone to be built up in successive layers.

Summary This data provided herein is based in part on a Phase II exploratory study examining the efficacy of misoprostol in the treatment of moderate-to-advanced periodontitis. These results indicate that misoprostol provides an important non-invasive step in the algorithm to treat these patients. None of the patients who received pretreatment with doxycycline followed by topical application of misoprostol alone for 6 weeks showed regression of the initial improvements one full year after treatment. Importantly, none of the patients who received misoprostol required surgical intervention to stop the progression of the disease. Finally, it was unexpectedly discovered that an even greater decrease in pocket depth and a decrease in teeth mobility was obtained when the mammalian (human) patients were pretreated with a systemic regimen of an antibiotic having activity against plaque producing bacteria and subsequently treated for three weeks with a pharmaceutical composition comprising both misoprostol and an antibiotic topically administered to, at, on, onto, in, into or near the periodontal pocket. See Table 6. The ability to reduce the treatment period from six (6) weeks to three (3) weeks is significant because not only did it provide superior results but it also insured a greater likelihood that patients would comply with the treatment regimen so as to receive the full benefit of the treatment.

Tomar, S. L., Asma S. Smoking-Attributable Periodontitis in the United States: Findings From NHANES III. J Periodontol 2000, 71: 743-751 has estimated that 9.2% of dentate adults develop periodontitis (pocket depths 4 mm), which projects to about 15 million cases of periodontitis among U.S. adults. With these large numbers of adult patients presenting for treatment, the addition of effective non-surgical interventions using oral medications would be advantageous based on ease of administration, minimal invasiveness and cost. In our opinion, the combination of misoprostol and an appropriate antibiotic has tremendous potential in the treatment of periodontal disease.

Overall Conclusions Scaling, root planning and curettage provided an approximately 25%-30% reduction in pocket depth after 6 weeks, and that was maintained for at least one year.

Topical applications of misoprostol (12 µg/site QID) for 6-7 weeks in combination with doxycycline pre-treatment (100 mg BID/QD for 10 days) resulted in statistically significant improvements in pocket depths at 52 weeks post-treatment compared to doxycycline pre-treatment alone in patients with moderate-to-advanced periodontitis.

Topical applications of misoprostol (12 µg/site QID) for 6-7 weeks, with and without doxycycline pre-treatment (100 mg BID/QD for 10 days), resulted in statistically significant improvements in pocket depths at 52 weeks post-treatment compared to the standard treatment in the art (i.e., scaling, root planning and curettage) in patients with moderate-to-advanced periodontitis.

At 52 weeks post-treatment, the improvements in pocket depths following pre-treatment with doxycycline (100 mg BID/QD for 10 days) followed by post-treatment with misoprostol (12 µg/site QID) for 6-7 weeks were numerically greater than improvements following the standard treatment in the art (i.e., scaling, root planning and curettage) followed by post-treatment with misoprostol (12 µg/site QID for 6-7 weeks) alone.

Doxycycline pre-treatment alone prior to the scaling, root planning and curettage procedure provided a short-term enhancement of reduction in pocket depth. Most of the effect can be ascribed to reduction in soft tissue inflammation and edema associated with reduction in the bacterial colonization and infection. However, doxycycline pre-treatment prior to the scaling, root planning and curettage procedure failed to provide any additional benefit at 52 weeks post-treatment beyond that provided by the scaling, root planning and curettage alone.

Misoprostol, applied locally in low doses (12 µg/site QID) for 6-7 weeks, resulted in the enhancement of the benefits of scaling, root planning and curettage. Initial effects in reducing pocket depth are detectable by 6 weeks, especially for deeper pockets and persist for 52 weeks.

The combination of systemic doxycycline pre-treatment and topical misoprostol post-treatment for 6-7 weeks resulted in recovery pattern characterized by a rapid onset (i.e., detectable at 6 weeks) and continued improvement over the long term (i.e., 52 weeks).

Misoprostol post-treatment, but not doxycycline pre-treatment, is characterized by decreases in tooth mobility, along with the decreases in pocket depth.

Unexpectedly superior results were obtained by systemically pretreating the patient with an antibiotic, such as doxycycline (100 mg BID/QD for 10 days), prior to topically administering misoprostol for 6 weeks to the periodontal pocket. Even more exceptional results were obtained in a shorter time (3 weeks) when the topically administered misoprostol was co-administered with a topically administered antibiotic, particularly in the same topical formulation. As reflected in Table 6, the mean change (decrease) in pocket depth for patients presenting baseline pocket depths of 15 mm was a 7.7 mm decrease for patients pretreated systemically with an antibiotic and topically treated with misoprostol for 6 weeks, or a 9.13 mm decrease for patients pretreated systemically with an antibiotic and topically treated with misoprostol and an antibiotic alone for only 3 weeks. Similar results appear in Table 6 for other baseline pocket depths as well. For example, the mean change (decrease) in pocket depth for patients presenting baseline pocket depths of 9 mm was a 4.04 mm decrease for patients pretreated systemically with an antibiotic and topically treated with misoprostol for 6 weeks, or a 4.96 mm decrease for patients pretreated systemically with an antibiotic and topically treated with misoprostol and an antibiotic alone for only 3 weeks.

The following examples illustrate the unexpectedly superior efficacy of the present pharmaceutical composition and method of treating periodontal disease with said pharmaceutical compositions in accordance with the instant invention.

DESCRIPTION OF THE PREFERRED EMBODIMENTS

The following examples are provided for illustrative purposes and are not to be construed to limit the scope of the claims in any manner whatsoever.

EXAMPLE 1

Comparative Study on Effects of Administering Misoprostol or Doxycycline Alone or in Combination 1.1 Overall Study Design and Plan This was a randomized, double-blind, single-center, multiple-dose, parallel-group, placebo-controlled study. At baseline, patients presenting at Periodontal Specialists of Ames for the treatment of periodontitis were screened for the study. Patients were assessed using medical histories, dental histories, blood pressure, pulse, pregnancy tests (if female), periapical radiographs and periodontal examinations. Patients who met all of the inclusion and exclusion criteria, appeared in good health other than periodontitis, and who had documented moderate-to-advanced periodontitis with at least four destructive periodontal-diseased pockets (ranging from 5 to 12 mm in depth) were eligible for study participation. Each patient underwent a gross debridement, following which, he/she was randomized to one of four treatment groups:

| Treatment Group | Assigned Treatment |
|---|---|
| A | Placebo |
| B | Doxycycline 100 mg BID/QD for ten days pre-treatment |
| C | Doxycycline 100 mg BID/QD for ten days pre-treatment + Misoprostol 10 ug/site QID for six weeks post-treatment |
| D | Misoprostol 10 ug/site QID for six weeks post-treatment |

Patients randomized to receive doxycycline (Groups B and C) were administered a loading dose of doxycycline 100 mg BID for one day and then instructed to take doxycycline 100 mg QD for nine consecutive days; patients in Groups A and D received matching doxycycline placebo for ten days.

On the last day of doxycycline/placebo administration, patients reported to the clinical research facility and underwent (under local anesthesia) dental sub-gingival scaling, root planing, and curettage on one side of the mouth. Following completion of these procedures, patients randomized to misoprostol (Groups C and D) received an application of a misoprostol paste (10 ug/site) and those randomized to placebo (Groups A and B) received placebo paste. Patients were instructed to apply the paste to each quadrant four times daily for the next week. One week later, patients returned to the clinical research facility and underwent sub-gingival scaling, root planing, and curettage on the other side of the mouth. The misoprostol/placebo paste was administered as described above. Patients were instructed to apply the paste to the affected teeth four times daily for an additional six weeks. They were also instructed to the proper use of the rubber tip for six weeks.

At two weeks post-treatment, patients were contacted for adverse event monitoring and compliance with study drug administration. Six weeks following the second sub-gingival scaling, planing, and curettage procedure, patients returned to the clinical research facility for periodontal and adverse event assessments. Dental prophylaxis, including periodontal maintenance was repeated at the three month intervals, with final assessments performed at 52 weeks post-treatment.

1.2 Discussion of Study Design, Including Choice of Control Groups Previous experience using misoprostol with periodontal regeneration in this facility has indicated a greater response when doxycycline was administered prior to scaling. Therefore, treatment arms using doxycycline alone, misoprostol alone, and misoprostol and doxycycline were included to investigate the synergistic effect of these drugs. The use of placebo did not endanger the patients and is considered standard in an efficacy trial. The treatment schedule is also considered standard practice for the treatment of periodontitis.

1.3 Study Population A total of 52 patients (13 per treatment group) were to be enrolled into the study. Patients meeting all of the inclusion criteria and none of the exclusion criteria were eligible for study participation.

1.3.1. Inclusion Criteria Patients were to meet all of the following inclusion criteria to enter the study:

1. Signed the basic consent form after reading the information summary.
2. Moderate to advanced localized chronic adult periodontitis, at least 20 natural teeth, and at least four periodontal pockets with probing pocket depths between 5 mm and 12 mm. There should not have been periodontal pockets where the depth of the pocket corresponded to the apex of the tooth as it might have developed an endodontic/periodontic combined lesion.
3. Evidence of crestal interdental bone loss in baseline periapical radiographs.
4. Class III or Class IV periodontal diagnosis, as determined by the standards of the American Academy of Periodontology.
5. Age between 19 and 75 years and in good systemic health as determined by a complete medical history, blood pressure and pulse rate measurements.
6. Ability to follow instructions for dental hygiene and ability to return for specified examinations.

1.3.2. Exclusion Criteria Patients were to be excluded from the study if any of the following conditions were present:
1. Periodontitis treatment within six months prior to the baseline exam.
2. Compromised heart condition that required antibiotic prophylaxis for prevention of infective endocarditis during dental procedures.
3. Joint replacement prostheses requiring antibiotic prophylaxis.
4. Previous or concurrent cancer treatment.
5. Evidence of compromised kidney function in medical history
6. Evidence of acute or chronic systemic infection such as herpes simplex, tuberculosis, AIDS in medical history.
7. Evidence of clinically significant chronic systemic disease such as cardiovascular disease, uncontrolled diabetes mellitus, hepatitis, lupus in medical history.
8. History of, or current clinical signs of, oral candidiasis.
9. Allergies to ingredients within the test and/or placebo agents.
10. Medication use that could have caused gingival enlargement, such as dilantin, cyclosporin, nifedipine, etc.
11. Antibiotic use within the past six months or concurrent antibiotic use.
12. Current non-steroidal anti-inflammatory drug use, or within one month of baseline exam.
13. Use of dentrifirice or rinses containing chlorhexidine or sanguinaria within one month of baseline exam.
14. Receipt any other investigational drug or device.
15. In the examiner's opinion, inability to comply with the instructions of the study.
16. Evidence of pulpitis.
17. Patients with bruxism who could not/would not wear a mouth guard.
18. Current use of tobacco products.
19. Pregnant women, women with a positive serum pregnancy test completed 10 days prior to study entrance, and childbearing age women not using non-hormonal (barrier) methods of contraception.
20. Acute periodontal infections.

1.3.3 Removal of Patients from Therapy or Assessment Patients were to be withdrawn from the study if a particular site lost more than 2 mm of attachment at any of the post-treatment examinations. Patients were also to be withdrawn if the plaque index, a measure of post-treatment protocol noncompliance, had a score of >0 after the screening exam.

If an individual tooth developed pulpitis post-treatment, the data for that tooth were excluded from the analysis. The patient was allowed to remain in the study, and all data for the remaining evaluable teeth were used in the analysis.

1.4 Treatments 1.4.1 Treatments Administered

Patients were randomized to one of four treatments:

| Treatment Group | Treatment Group Assignment | Study Medications Administered | |
|---|---|---|---|
| | | Pre-treatment | Post-treatment |
| A | Placebo | Placebo BID for 1 day, followed by QD for 9 days | Placebo Paste QID for 6–7 weeks |
| B | Doxycycline | Doxycycline 100 mg BID for 1 day, followed by 100 mg QD for 9 days | Placebo Paste QID for 6–7 weeks |
| C | Doxycycline + Misoprostol | Doxycycline 100 mg BID for 1 day, followed by 100 mg QD for 9 days | Misprostol paste 10 ug/site QID for 6–7 weeks |
| D | Misoprostol | Placebo BID for 1 day, followed by QD for 9 days | Misprostol paste 10 ug/site QID for 6–7 weeks |

Doxycycline and doxycycline placebo were administered orally. The misoprostol and placebo pastes were administered topically.

1.4.2 The Pharmaceutical Agents Commercially-produced doxycycline 100 mg capsules (lot number KH7-073-Medisca), and commercially-produced misoprostol 200 µg tablets (lot numbers 68N643, 68H623, 8P649, 9M671, 9H675-Searle) were obtained from their respective manufacturers.

Doxycyline was overencapsulated in #3 yellow/gray gelatin capsules (lot number 62371) in order to maintain the study blind. Empty capsules were used for the doxycycline placebo.

The misoprostol and placebo pastes were prepared by a pharmacist. The misoprostol tablets were ground to a fine powder and prepared as described below.

For the misoprostol paste, misoprostol was mixed with polyethylene glycol flakes (carbowax), polyethylene glycol, SUPER WERNET'S® Denture Adhesive Powder and absolute ethanol to a final concentration of 50 ug/ml. The mixture was loaded into 10 ml syringes by the staff pharmacist; this provided a total of 50 application sites per syringe.

For the placebo paste, the mixture of polyethylene glycol flakes (carbowax), polyethylene glycol, SUPER WERNET'S® Denture Adhesive Powder and absolute ethanol was loaded into 10 ml syringes by the staff pharmacist; this provided a total of 50 application sites per syringe.

1.4.3 Method of Assigning Patients to Treatment Patients were randomly assigned to each treatment by the University of Iowa Dental School staff pharmacist, Karen Baker. The pharmacist assigned each patient-a number between 1 and 72 and labeled all study medications for that patient with the appropriate number.

1.4.4 Selection of Doses in the Study The doxycycline regimen use in this study is considered standard practice for periodontitis treatment. The misoprostol dose used in the study was based on the Investigator's previous experience in the clinic with treatment of aphthous ulcers and lichen planus with misoprostol.

1.4.5 Timing of Dose for Each Patient Doxycycline and matching placebo were administered orally on a daily basis for ten days, without regard to standard water or food intake. Patients were instructed to take medication at approximately the same time each day.

The initial dose of the misoprostol/placebo paste was applied by the periodontist, and all subsequent doses were applied by the patient. Each affected tooth was wiped with a 2×2 sponge to dry the tissue. Then 0.2 ml of the paste was dispensed from the 10.0 ml syringe onto the tip of the finger and applied to each affected tooth. The patient then sipped a little water and gently flushed the paste to gel it. Patients were instructed not to eat anything for at least one hour.

1.4.6 Blinding This was a double-blind study. All study medications were prepared and labeled with a number code; this code, which corresponded to the patient's assigned treatment, was not known to the Applicants, any other study site personnel, or study patients. Overencapsulation was used to maintain the blind for doxycycline.

1.4.7 Prior and Concomitant Therapy Concomitant medications were allowed during the study. Patients were encouraged not to change the dosage regimen during the 7-week treatment period. Concomitant medication use during the 52-week follow-up period was not monitored.

1.4.8 Treatment Compliance Treatment compliance was assessed by questioning the patient about the application of the study medication. Quantitative assessments of treatment compliance were not performed.

1.5 Efficacy and Safety Variables 1.5.1 Efficacy and Safety Measurements Assessed Efficacy was assessed using periodontal examinations and periapical radiographs. Safety was assessed primarily through adverse event monitoring. The schedule of observations and procedures is presented in Table 1.

adherence to the manufacturer's guidelines with regard to time and temperature control. All conventional radiographs were illuminated and digitized using an Imapro QCS 3200 flat bed scanner (Imapro Corp, Ogdensburg N.Y.) with a pixel spatial resolution of 0.042 mm and an 8-bit gray scale depth. The QCS 3200 provided a lamp drift of less than 2% over a scan. All radiographic images were archived on optical disks. Crestal bone height was measured using periapical radiographs for posterior teeth and anterior teeth. At least four sites showing pocket depth of 5-12 mm were selected for each patient. For these x-rays, stepwedges were used for contrast and density correction. Two radiographic images for each anatomic site was projected on the computer monitor when making crestal bone height measurements. This "side-by-side" image projection provided greater consistency in the identification of reference landmarks.

In order to assess any changes in alveolar crestal height, cemento-enamel junction (CEJ) to alveolar crest distance measurement was made mesially and distally, parallel to the long axis for each tooth on each set of two images.

Radiographs were digitally enhanced using the Adobe Photoshop Adjust Levels tool. This allowed the digital

TABLE 1

Schedule of Observations and Procedures

| Procedure | Baseline −10 days | Day 1 | 1 Wk | 2 Wk | 6 Wk (a) | 3 Mo | 6 Mo | 9 Mo | 12 Mo (b) |
|---|---|---|---|---|---|---|---|---|---|
| Medical History | X | | | | | | | | |
| Dental History | X | | | | | | | | |
| Blood Pressure, Pulse | X | X | X | X | X | X | X | X | X |
| AAP Classification | X | | | | | | | | |
| Pregnancy Test | X | | | | | | | | |
| Periodontal Exam | | | | | | | | | |
| Pocket Depth | X | | | | X | X | X | X | X |
| Bleeding | X | | | | X | X | X | X | X |
| Attachment Level | X | | | | X | X | X | X | X |
| Plaque Index | X | | | | X | | | | |
| Periapical Radiograph | X | | | | X | | | | X |
| Gross Debridement | X | | | | | X | X | X | X |
| Sub-Gingival Scaling and Planing | X | X (c) | X (c) | | | X | X | X | X |
| Doxycycline/Placebo Administration (d) | X | X | | | | | | | |
| Misprostol/Placebo Administration (e) | | X | ⟶ | X | | | | | |
| Adverse Event Monitoring | | X | X | X | X | X | X | X | X |

(a) Relative to second scaling and planing procedure.
(b) Study blind was broken at 52 weeks. Patients who had not received misoprostol were offered the option to enroll in a six-week open-label extension in which they received misoprostol for six weeks.
(c) Procedure performed on one half of the mouth on Day 1 and the other half of the mouth one week later.
(d) Initiation of doxycycline for 10 days prior to scaling/planing on Day 1; last dose completed on Day 1.
(e) Administered four times daily for a total of 6 weeks on one side of the mouth and 7 weeks on the other side.

1.5.1.1. Periapical Radiographs Four periapical radiographs using stepwedges were performed at baseline, 6 weeks and 52 weeks. Stepwedges were used to maintain accuracy at recall intervals. Kodak Ultra-speed (D-speed) film was used (Eastman Kodak Co., Rochester N.Y.). Film exposures were made under standard setting of 70 kVp, 15 mA, 16 inch fixed focal image distance (FID). These exposure settings were maintained throughout the course of the study. All dental radiographs were processed manually using freshly mixed Kodak GBX developer and fixer with strict images to all have roughly the same range of contrast and brightness. Performing just the normalization improved the qualitative comparison of the images by standardizing (from image to image)the gray scales that represent the different tissue types.

Once normalized, additional enhancements of the images were performed. One simple technique was to assign colors to the gray scales (pseudo coloring). This technique takes advantage of the fact that our vision is more sensitive to changes in color than in changes in gray scale. These pseudo colored images make it much easier to discriminate differences between radiographs.

Another enhancement technique was to combine a threshold, inverted image with the normalized image. This was done using a multiplication operation in the layers palette of Photoshop. This operation enhanced the region of the treatment area.

Bone density was estimated using semi-quantitative techniques where gray scale values in the digital images were calibrated to a rough bone density scale. To do this, a region in a bone- (or tissue)-free region of the radiograph was defined and it's mean gray scale was defined as the zero-density point. Then a region in a carie or other bright point in the radiograph was defined and it's mean gray scale was defined as the 100% dense point. Using these two points a scale linking gray scale measurements to bone density was constructed and applied to measurements of regions defined in the treatment area.

These bone density measurements and pseudo coloring were done with Image J a program developed by Wayne Rasband at the Research Services Branch, National Institute of Mental Health, Bethesda, Md. Adobe Photoshop version 6.0 was used for normalization and gray scale operations.

1.5.1.2. Periodontal Examination by 1.5.1.2.1. Periodontal Pocket Probing Depth Periodontal probing depths were measured at baseline, at six weeks post-treatment, and at 3, 6, 9 and 12 months post-treatment. More recently, a larger study at three weeks post treatment was performed as described in Example To measure the periodontal pocket probing depth, a manual University of Michigan off-set probe marked in millimeters was inserted into the pocket with the long axis parallel to the long axis of the tooth. Insertion was continued to the base of the pocket with gentle pressure until a distinct resistance was felt.

The measurement from the tip of the probe to the gingival margin (GM-BP, gingival margin to the base of the pocket) was recorded in millimeters. On measurements of proximal sites the gingival margin may cross the probe at an angle, and the highest point on the side of the probe was read. If the distance fell between two probe graduations, the number was rounded to the nearest whole numbers. Pocket measurements were recorded at the following six sites around the tooth:

| | |
|---|---|
| Mesio-buccal | with side of probe touching both teeth in embrasure near the contact point. If there was no adjacent tooth, the probe must have been aligned at the line angle of the tooth. |
| Mid-buccal | If the tooth was rotated, measurements were made in the middle of the exposed surface and not at the anatomical middle of the tooth. |
| Disto-buccal | with the side of the probe touching both teeth in the embrasure near the contact point. If there was not adjacent tooth the probe was to be aligned at the line angle of the tooth. |
| Mesio-lingual | with the side of the probe touching both teeth in the embrasure near the contact point. If there was no adjacent tooth, the probe was to be aligned at the lie angel of the tooth. |
| Mid-lingual | if the tooth was rotated, the measurement was done in the middle of surface and not at the middle of the anatomic mid-lingual. |
| Disto-lingual | with the side of probe touching both teeth in the embrasure near the contact point. If there was no adjacent tooth, the probe was to be aligned at the line angle of the tooth. |

In measuring the pockets, the long axis of the probe was kept as parallel to the long axis of the tooth as possible.

1.5.1.2.2. Bleeding Upon Probing Bleeding upon probing was assessed at baseline, at six weeks post-treatment, at 3, 6, and 9 months post-treatment, and at 52 weeks (12 months) post-treatment. After removing the probe from a pocket, the site was observed and scored from 0-3 as follows:

| | |
|---|---|
| 0 | No Bleeding |
| 1 | A small point of blood seen at the probe exit site, or a very thin line of blood |
| 2 | Bleeding that filled the interdental embrasure or ran along margin as more than a thin line |
| 3 | Profuse bleeding seen immediately after probe removal |

1.5.1.2.2. Probing Attachment Level Attachment levels were measured at baseline, at six weeks post-treatment, at 3, 6, and 9 months post-treatment, and at 52 weeks (12 months) post-treatment. To measure the probing attachment level at fixed reference was used as a landmark. The cemento-enamel junction (CEJ) was located by placing the periodontal probe against the enamel surface coronally to the gingival margin and with the probe at about 45 degrees to the long axis, the tip was moved axially along the enamel until a change in direction of "bump" was felt at the CEJ.

If the gingival margin was on enamel, the measurement from the probe tip to the GM (GM-CEJ) was recorded as a positive number.

If the gingival margin was on the root, the measurement from the CEJ to the gingival margin was recorded as a negative number. The GM-CEJ was subtracted from the GM-BP to determine the probing attachment level. If the CEJ was not clearly detectable, then the incisal edge (Landmark X) or a restoration margin (landmark R) may have been used. Landmark X data were negative numbers. Landmark R data were negative numbers if the restoration margin was coronal to the gingival margin. It was better to use an R landmark than an uncertain CEJ.

1.5.1.2.3. Plaque Index Plaque index was measured and graded at baseline and six weeks post-treatment using the following criteria:

| | |
|---|---|
| 0 | No plaque in the gingival area |
| 1 | A film adhering to the free gingival margin and adjacent area of the tooth |
| 2 | Moderate accumulation of soft deposits within the gingival pocket on the gingival margin and/or adjacent tooth surface that could be seen by the naked eye |
| 3 | Abundance of soft matter within the gingival pocket and/or on the gingival margin and adjacent tooth surface |

1.5.1.3. American Association of Periodontology Classification Based on periodontal examinations and periapical radiographs, only patients with Class III or Class IV periodontal classifications were eligible for enrollment in the present study.

| Class | Type | Symptoms |
|---|---|---|
| I | Gingivitis | No attachment loss |
| | | Bleeding may or may not be present |
| | | Pseudopockets may be present |
| | | Only the gingival tissues have been affected by the inflammatory process |

-continued

| Class | Type | Symptoms |
|---|---|---|
| II | Early Periodontitis | Bleeding upon probing may be present in the active phase<br>Pocket depths or attachment loss of 3 to 4 mm<br>Localized areas of recession<br>Possible Class I furcation invasion areas<br>Horizontal type of bone loss is most common<br>Slight loss of the interdental septum<br>Alveolar bone level is 3 to 4 mm from the CEJ area |
| III | Moderate Periodontitis | Pocket depths or attachment loss of 4 to 6 mm<br>Bleeding upon probing<br>Grade I and/or Grade II furcation invasion areas<br>Tooth Mobility of Class I<br>Horizontal or Vertical bone loss may be present<br>Alveolar bone level is 4 to 6 mm from the CEJ area<br>Radiographic furcations of Grade I and/or Grade II<br>Crown to root ratio is 1:1 (loss of ⅓ of supporting alveolar bone) |
| IV | Advanced Periodontitis | Bleeding upon probing<br>Pocket depths or attachment loss over 6 mm<br>Mobility of Class II or Class III<br>Horizontal and vertical bone loss<br>Alveolar bone level is 6 mm or more from the CEJ area<br>Radiographic furcations<br>Crown to root ratio is 2:1 or more (loss of over ⅓ of the supporting alveolar bone) |

1.5.1.4. Adverse Events Patients were queried for adverse events at all study visits. In addition, patients were instructed to call the study site to report any adverse side effects of the study medication.

1.5.1.5. Vital Sign Measurements Blood pressure and pulse measurements were taken at all study visits to ensure patients were in good health. These data were not entered into the database.

1.5.1.6. Appropriateness of Measurements The measurements performed in this study are considered standard practice for the treatment of periodontitis.

1.6 Data Quality Assurance To ensure consistent measurements, all periodontal assessments were performed by the Principal Investigator. Data were entered into an Excel database and a 100% audit of the pocket depth data was performed.

1.7 Statistical Methods and Determination of Sample Size 1.7.1 Statistical and Analytical Methods All analyses are performed using the NPAR1WAY or TTEST procedures in SAS. Plots are created using MINITAB.

1.7.1.1 Efficacy Analyses Mean changes in pocket depth were determined at 6 and 52 weeks post-treatment. Patients presented with baseline pocket depths of 4, 5, 6, 7, 8, 9, 10, 12, and 15 millimeters. Separate analyses were performed for each baseline pocket depth between 4 and 10 mm; however, due to small sample sizes, analyses were not performed for the remaining baseline pocket depths. Mean changes in pocket depths were calculated per patient and per measurement. Standard deviations for patient means were presented, however, since a positive correlation was expected between the change in pocket depth for the same patient, standard deviations were not reported for these measurements. In order to evaluate the normality of the distribution of the patient means, skewness and kurtosis values, which are equal to 0 for a normal distribution, were presented.

Pairwise comparisons were performed using the nonparametric Wilcoxon rank-sum test. The test assumes that either the two treatment distributions are equal or one distribution is stochastically larger than the other. These assumptions are much weaker than the assumption of normal distributions with equal variance. Dot plots for each sample were inspected for any serious violations of these assumptions. The reported Wilcoxon rank-sum test p-values were based on the exact distribution of the test statistic.

For completeness, pairwise comparisons were also performed using the unequal variances t test. We used the unequal variances t procedure rather than the equal variances t procedure since ratios of the standard deviations of the samples varied by as much as 3 to 4 in some cases.

The primary efficacy analysis was comparisons between doxycycline alone and doxycycline+misoprostol in mean changes in pocket depths at 52 weeks post-treatment. No multiple-comparison correction was used, since these were considered to be a priori hypotheses and there were only 7 a priori hypotheses.

All other pairwise comparisons were considered secondary analyses. The secondary analyses were considered to be exploratory in nature, and multiple-comparison correction procedures were not used in order to detect all clinically meaningful differences. However, we recognize that conclusions drawn from these analyses must be verified by future research.

1.7.1.2 Safety Analyses No formal analyses were performed on any of the safety parameters.

1.7.2 Determination of Sample Size In a previous study (Hill, R W, Ramfjord, S P, Morrison, E C, Appleberry, E A, Caffesse, R G, Kerry, G J, and Nissle, R R., Four types of periodontal treatment compared over two years, J. Periodontol 51981, 2: 655 (1981)), patients receiving scaling and root planing only and having pockets greater than or equal to 7 mm had a mean change in pocket reduction from baseline of 2.85 mm with a standard deviation of 1.91 mm after one year. Since similar patients treated herein with Cipro® (ciprofloxacin) & Flagyl® (metronidazole) plus misoprostol with scaling and root planing treatment showed an average exceeding 5.85 mm, we used 3 mm as our effect size, we would need 10 patients in each group in order to achieve a power of 0.9 to detect a 3 mm difference between treatments; this computation is based on a two-sample t test with a 0.05 two-sided significance level and assumes a common standard deviation of 1.91. This computation was performed using the nQuery Advisor 4.0 software. In order to allow for dropouts and for variability in the mean reduction and standard deviation estimates, the sample size was increased to 13.

2.0 Study Patients 2.1 Disposition of Patients In an initial study, a total of 58 patients were enrolled; 58 patients were remaining in the study at 6 weeks post-treatment and 40 patients were remaining in the study at 52 weeks post-treatment.

2.2 Protocol Deviations In the initial study, Patient 51 who was randomized to receive placebo+misoprostol, mistakenly received placebo+placebo. The error occurred at the University of Iowa Dental School Pharmacy. The pocket depth data for this patient showed much less improvement than other patients in the placebo+misoprostol group. However, the dosing error was not discovered until after the statistical analysis had been performed and, therefore, all data for this patient were included in the statistical analysis for the placebo+misoprostol group.

3.0 Efficacy Evaluation 3.1 Data Sets Analyzed All available data were used in the efficacy summaries (N=58 at six weeks and N=40 at 52 weeks).

TABLE 2

Patients Excluded from the Efficacy Analyses

| Assessment | Placebo | Doxycycline | Doxycycline + Misoprostol | Misoprostol |
|---|---|---|---|---|
| 52 Weeks Post-treatment | 1, 32, 33, 64 | 10, 21, 54, 60, 70 | 14, 22, 40, 50, 58 | 28, 35, 59, 71 |

3.2 Demographics and Other Baseline Characteristics
Enrolled patients ranged in age from 34 to 77 years, and mean ages ranged from 50.1 to 53.4 years across the treatment groups (Table 3). Patients were primarily Caucasian (85.7% in each treatment group), and except for the doxycycline+misoprostol group, gender was fairly evenly distributed. All of the patients had a Class III AAP diagnosis.

TABLE 3

Demographics and Baseline Characteristics

|  | Placebo N = 14 | Doxycycline N = 15 | Doxycycline + Misoprostol N = 15 | Misoprostol N = 14 | P-Value (a) |
|---|---|---|---|---|---|
| Age (yr) | | | | | |
| Mean ± SD | 51.9 ± 10.58 | 50.1 ± 7.07 | 50.2 ± 8.95 | 53.4 ± 7.10 | 0.12 |
| Range | 37-77 | 34-66 | 37-67 | 40-65 | |
| Gender (N, %) | | | | | |
| Males | 8 (57.1%) | 6 (40.0%) | 12 (80.0%) | 6 (42.9%) | 0.69 |
| Females | 6 (42.9%) | 9 (60.0%) | 3 (20.0%) | 8 (57.1%) | |
| Race (N, %) | | | | | |
| White | 12 (85.7%) | 15 (100.0%) | 13 (86.7%) | 14 (100.0%) | |
| Black | 2 (14.3%) | 0 (0.0%) | 1 (6.7%) | 0 (0.0%) | |
| Unknown | 0 (0.0%) | 0 (0.0%) | 1 (6.7%) | 0 (0.0%) | |
| AAP Diagnosis (N, %) | | | | | |
| Class III | 14 (100.0%) | 15 (100.0%) | 15 (100.0%) | 14 (100.0%) | |
| Class IV | 0 (100.0%) | 0 (100.0%) | 0 (100.0%) | 0 (100.0%) | |

(a) ANOVA for comparison of age and Pearson chi-square test for comparison of proportion of males.

3.3 Measurements of Treatment Compliance No quantitative measurements of treatment compliance were performed. All patients were provided four 10.0 ml syringes of study medication containing sufficient quantities of study medication for the six-week post-treatment period. Patients were queried at one, two and six weeks post-treatment concerning administration of the study medication. However, 10 patients reported that they did not have sufficient medication for the entire six-week postdosing interval and were provided additional syringes of misoprostol paste (Table 4).

TABLE 4

Additional Study Medication

| Treatment (a) | Patient | Additional Syringes |
|---|---|---|
| A | 33 | 2 |
| A | 63 | 1 |
| A | 68 | 2 |
| B | 49 | 2 |
| B | 65 | 2 |
| C | 6 | 2 |
| C | 40 | 2 |

TABLE 4-continued

Additional Study Medication

| Treatment (a) | Patient | Additional Syringes |
|---|---|---|
| D | 35 | 2 |
| D | 46 | 2 |
| D | 71 | 2 |

3.4 Efficacy Results and Tabulations of Individual Patient Data 3.4.1 Efficacy Results Descriptive statistics for the change in pocket depth after 6 and 52 weeks for each group and baseline depth are displayed in the end-of-text Tables 1 and 2 and Table 5. Plots of the mean changes per observation and per patient are displayed respectively in FIGS. 1A and 1B (6 weeks) and in FIGS. 1C and 1D (52 weeks).

3.4.1.1 Pocket Depth Changes Mean changes in pocket depth were determined for each observation for each patient. Similar results were obtained using the two methods (FIGS. 1A-1D). At six weeks post-treatment, all three active treatments had a greater effect on pocket depth than placebo; however, at 52 weeks post-treatment, the misoprostol groups (placebo+misoprostol and doxycycline+misoprostol) had greater effects than doxycycline+placebo or placebo.

Due to a dosing error, one patient (51) in the placebo+misoprostol group received placebo+placebo. Since the statistical analysis was performed using an intent-to-treat cohort, all data for this patient were included in the summary statistics and statistical analyses for the placebo+misoprostol group.

For the primary comparison between doxycycline+placebo and doxycycline+misoprostol, administration of doxycycline+misoprostol resulted in statistically significantly greater mean changes in pocket depths compared to doxycycline+placebo at 52 weeks post-treatment for pockets having baseline depths between 4 and 9 mm (Table 5).

TABLE 5

Summary of Mean Changes in Pocket Depths Using Patient as Inference

|  | 4 mm | 5 mm | 6 mm | 7 mm | 8 mm | 9 mm | 10 mm |
|---|---|---|---|---|---|---|---|
| 6 Weeks | | | | | | | |
| Placebo | 0.56 | 1.34 | 1.72 | 1.99 | 2.39 | 2.79 | 3.29 |
|  | N = 1433/14 | N = 386/14 | N = 165/14 | N = 127/14 | N = 133/13 | N = 38/11 | N = 31/8 |
| Doxycycline | 0.84 | 1.96* | 2.63* | 3.04* | 3.57* | 4.23* | 4.13 |
|  | N = 1292/15 | N = 393/15 | N = 244/15 | N = 237/15 | N = 149/15 | N = 52/12 | N = 32/9 |
| Doxycycline + Misoprostol | 0.85 | 1.85* | 2.49* | 3.30* | 3.81* | 4.04 | 4.51 |
|  | N = 1533/15 | N = 385/15 | N = 176/15 | N = 161/15 | N = 142/14 | N = 45/13 | N = 24/12 |
| Misoprostol | 0.58 | 1.57 | 2.13 | 2.68 | 2.84 | 4.46* | 4.70 |
|  | N = 1573/14 | N = 242/14 | N = 130/14 | N = 97/13 | N = 86/14 | N = 29/11 | N = 19/10 |
| 52 Weeks | | | | | | | |
| Placebo | 0.10 | 0.86 | 1.43 | 1.77 | 1.90 | 2.22 | 3.18 |
|  | N = 993/10 | N = 286/10 | N = 131/10 | N = 105/10 | N = 95/9 | N = 29/7 | N = 28/6 |
| Doxycycline | −0.22* | 0.42 | 0.79 | 1.42 | 1.71 | 2.86 | 3.28 |
|  | N = 819/10 | N = 275/10 | N = 150/10 | N = 154/10 | N = 103/10 | N = 46/10 | N = 25/5 |
| Doxycycline + Misoprostol | 1.13*&† | 2.31*† | 2.98*† | 4.04*† | 4.89*† | 5.07*† | 5.52 |
|  | N = 970/10 | N = 270/10 | N = 130/10 | N = 123/10 | N = 117/10 | N = 35/10 | N = 13/8 |
| Misoprostol | 0.75*† | 1.76*† | 2.49† | 3.28*† | 3.90*† | 5.06*† | 4.75 |
|  | N = 1231/10 | N = 145/10 | N = 73/10 | N = 58/9 | N = 62/10 | N = 23/9 | N = 11/6 |

*p < 0.05 compared to placebo using Wilcoxon Rank-Sum test.
&p < 0.05 compared to misoprostol using Wilcoxon Rank-Sum test.
†p < 0.05 compared to doxycycline using Wilcoxon Rank-Sum test.
N given as Number of observations/Number of patients At six weeks post-treatment, there were no statistically significant differences between the active treatment groups for the mean changes in pocket depths. Both doxycycline+ placebo and doxycycline+misoprostol were statistically superior to placebo in the majority of the assessments (for baseline depths between 4 mm through 9 mm for doxycycline+placebo and between 4 mm through 8 mm for doxycycline+misoprostol).

At 52 weeks post-treatment, the only assessment showing statistical significance between doxycycline and placebo was for pocket depths 4 mm. As stated above, doxycycline+ misoprostol showed statistically significantly greater changes in mean pocket depths compared to doxycycline+ placebo in all assessments except for those having a baseline depth of 10 mm. Similar results were obtained when doxycycline+misoprostol was compared to placebo. When placebo+misoprostol was administered, mean changes in pocket depths were statistically superior to placebo and doxycycline treatments in the majority of the assessments. Although mean changes in pocket depths with doxycycline+ misoprostol were numerically superior to those for placebo+ misoprostol, only one (4 mm) of the assessments was statistically significantly different between treatments.

For baseline pocket depths 10 mm, 11 of 28 samples had a skewness exceeding 1 in magnitude and 10 samples have a kurtosis exceeding 2, suggesting that the normality assumption was not tenable (end-of-text Table 2). End-of-text FIGS. 3 and 4 did not reveal any serious violations of the Wilcoxon assumptions.

3.4.1.1.1 Effect of Doxycycline The graphs in FIG. 1 show that 6 weeks and 52 weeks after the scaling, root planning and curettage procedure, the patients showed a reduction in pocket depth, regardless of how deep the pocket was originally. Even in the placebo treatment group, pocket reductions were in the order of 25-30%, indicating that this basic approach. to treatment is beneficial, even though not as optimal as desired.

Figure 1B:
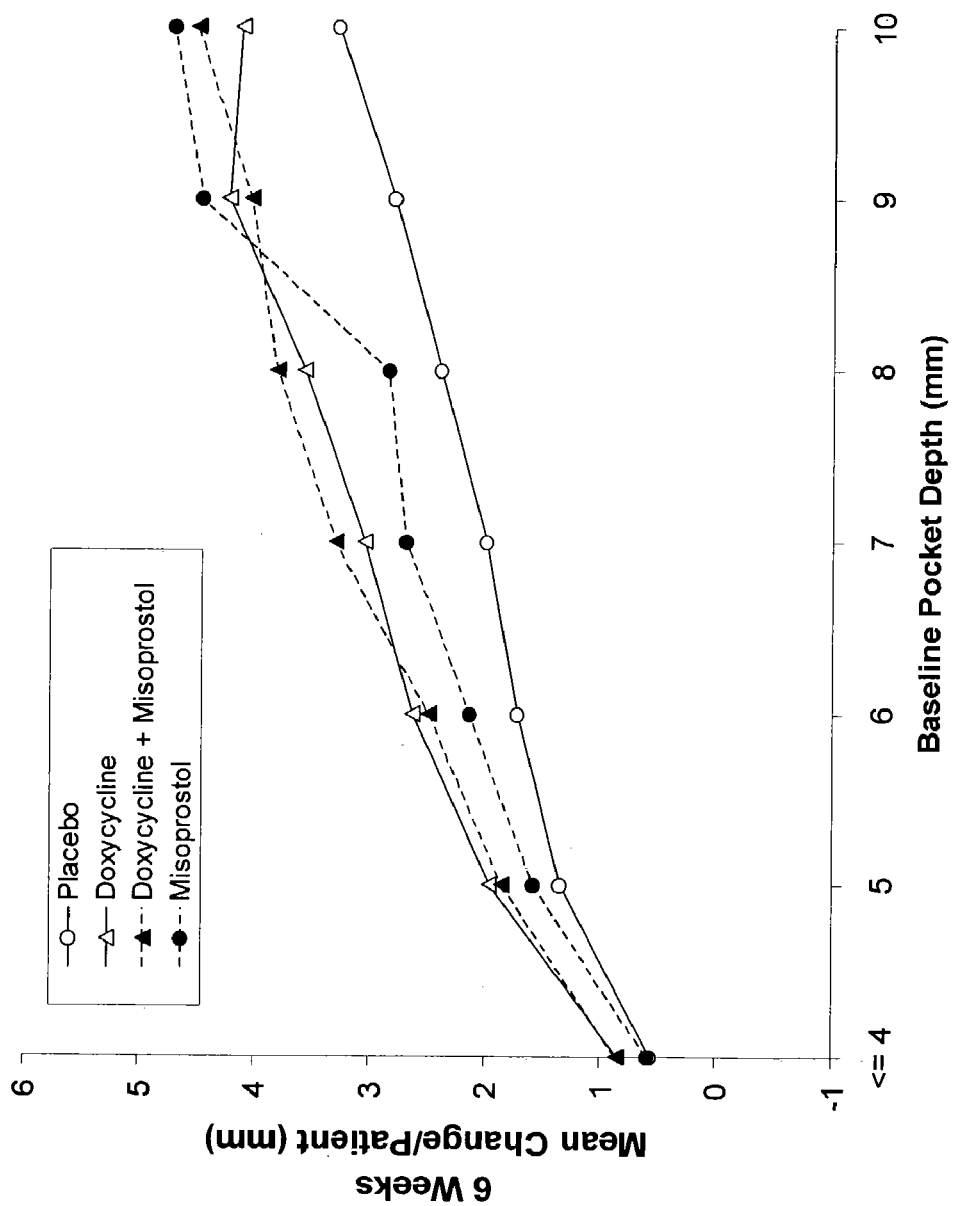
FIG. 1B is a comparative graph of the mean change in pocket depth (mm) per observation versus the baseline pocket depth (mm) at 52 weeks post-treatment for the following four treatment modalities: placebo (open circle); doxycycline (open triangle); doxycycline+misoprostol (shaded triangle); and misoprostol (shaded circle) for N=40.

The graphs in FIGS. 1A-1B show that 6 weeks after the scaling, root planing and curettage treatment session, the patients that were pretreated with doxycycline (with or without misoprostol treatment) have a greater decrease in their pocket depths than did patients receiving placebo. They also appeared to have a greater decrease in the pocket depths than did the patients receiving only misoprostol, except possibly when the original pockets depths were 10 mm and greater. (See end-of-text Table 1 for results on all pocket depths, including 12 mm and 15 mm.) The importance of the doxycycline pre-treatment on the 6-week status of the patients is consistent whether one looks at the data by observation site, or by the patient (which effectively combines the results of several observation sites).

Figure 1C:
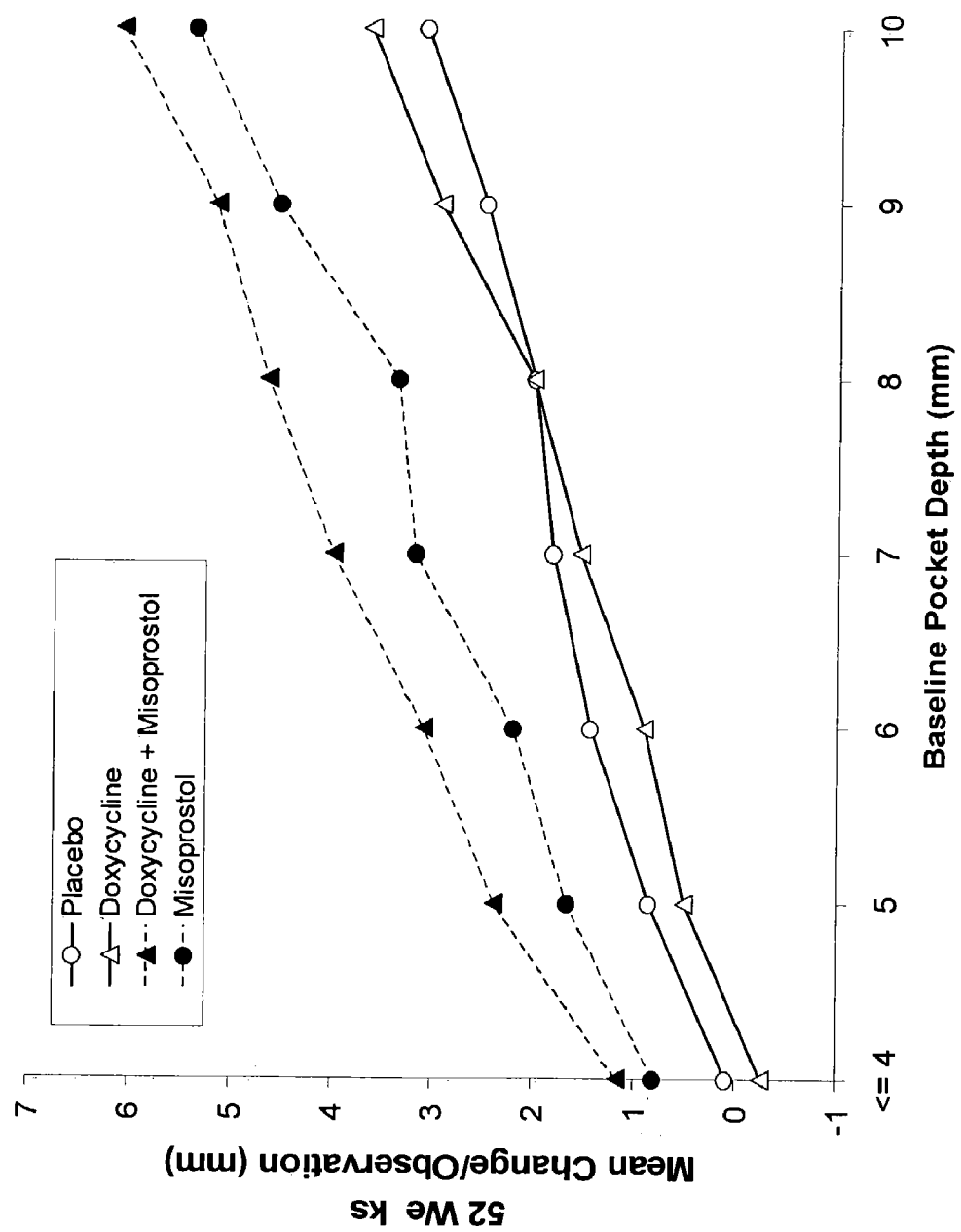
FIG. 1C is a comparative graph of the mean change in pocket depth (mm) per patient versus the baseline pocket depth (mm) at 6 weeks post-treatment: for the following four treatment modalities: placebo (open circle); doxycycline (open triangle); doxycycline+misoprostol (shaded triangle); and misoprostol (shaded circle) for N=58.
Figure 1D:
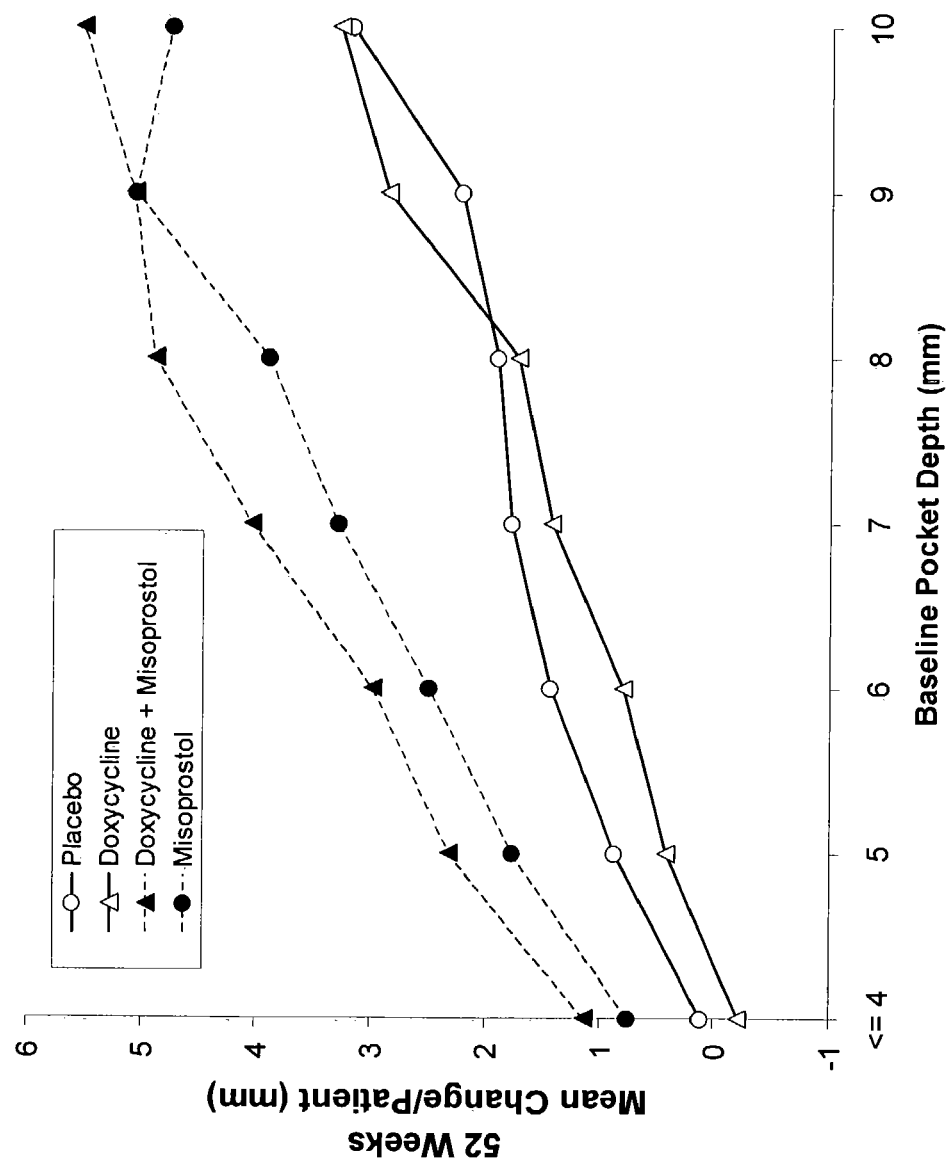
FIG. 1D is a comparative graph of the mean change in pocket depth (mm) per observation versus the baseline pocket depth (mm) at 52 weeks post-treatment for the following four treatment modalities: placebo (open circle); doxycycline (open triangle); doxycycline+misoprostol (shaded triangle); and misoprostol (shaded circle) for N=40.

As shown in FIGS. 1C and 1D, the added benefit of the doxycycline pre-treatment, while very apparent 6 weeks after stopping the treatment (FIGS. 1A and 1B), was not apparent 52 weeks after the scaling, root planing and curettage. Without an accompanying misoprostol treatment regimen, doxycycline pre-treatment did not have any additional long-term benefit in the control of the patients' periodontal disease beyond that of the standard scaling, root planing and curettage alone (placebo). A comparison between the FIGS. at 6 weeks (FIGS. 1A and 1B) and at 52 weeks (FIGS. 1C and 1D) show that part of the early benefit obtained with doxycycline was actually lost during the intervening 46 weeks. For instance, places were the pocket depth was originally 10 mm, showed a reduction in depth of nearly 5 mm at 6 weeks, but that improvement was not permanent, reverting to only a 3 mm improvement by Week 52.

3.4.1.1.2 Effect of Topical Misoprostol The two treatment groups that received misoprostol showed additional improvement beyond that provide by scaling, root planing and curettage alone. When examined 6 weeks after the scaling, root planing and curettage and after 6 weeks of local misoprostol administration, the misoprostol alone treatment appeared to be more beneficial as the pocket depth increased. In cases where the original pocket depth was 10 mm or greater, the reduction in pocket depth after 6 weeks was by 40-50%, and remained there even through to the one year observation point. The misoprostol applications were discontinued at the 6- or 7-week time point by the patients.

In patients that had the doxycycline pre-treatment before the scaling, root planing and curettage, and used the misoprostol applications for 6-7 weeks afterwards, the benefits were maximal among the treatments investigated. At the 6-week observation, the patients receiving the dual regimen performed as well as the doxycycline only patients. At the 52-week observation the patients receiving the dual regimen showed the greatest reduction in pocket depth of all groups. The dual regimen was the only treatment that resulted in a trend towards apparent continued improvement in pocket depth between the Week 6 and Week 52 observations. These patients had approximately 40-50% mean reductions in pocket depth at Week 6, and approximately 50-60% percent mean reduction at Week 52.

3.4.1.1.3 Effect on Pocket Depth of Topical Misoprostol and Doxycycline at 3 Weeks Post Treatment Versus Topical Misoprostol alone after 6 Weeks Post Treatment In a larger study, the change in pocket depth was determined for those patients presenting the inclusion criteria of Example 1.3.1 and none of the exclusion criteria of Example 1.3.2 after three (3) weeks of treatment with misoprostol and doxycycline (new data), as described herein, and was compared to the change in pocket depth at 6 weeks for those patients also treated with misoprostol and doxycycline (Group C patients of Example 1). The comparative data in Table 6 is reported as a function of the patient's baseline pocket depth (2 mm to 15 mm) prior to treatment. Table 6 reports each of the following: the number of observations (N_Obs), the mean change in pocket depth for all surfaces for all patients (i.e., all observations) having the specified baseline pocket depth ("mean of observation"), the number of subjects (N_subj), and the mean of the individual means ("mean of subject means") wherein an individual mean is the mean change for all surfaces for that individual having the specified baseline depth.

Based upon the Wilcoxon p-value, Table 6 reflects that the combination of misoprostol and doxycycline produced a statistically significant change (improvement) in pocket depth at three weeks versus 6 weeks for the subject patients.

TABLE 6

Change in pocket depth (mm) after 3 weeks topical cotreatment with misoprostol/antibiotic ("new data") compared with change after 6 weeks topical treatment with misoprostol (Group "C" herein)

| baseline depth (mm) | group | N_Obs | Mean change (mm) of observations | N_subj | Mean change (mm) of subject means | Wilcoxon p_value[1] |
|---|---|---|---|---|---|---|
| ≦2 | C | 71 | −0.03 | 6 | −0.03 | 0.4893 |
| ≦2 | New Data | 2863 | −0.01 | 34 | −0.01 | |
| 3 | C | 973 | 0.67 | 15 | 0.66 | 0.1710 |
| 3 | New Data | 1491 | 0.75 | 33 | 0.75 | |
| 4 | C | 509 | 1.34 | 15 | 1.29 | 0.0876 |
| 4 | New Data | 829 | 1.59 | 31 | 1.52 | |
| 5 | C | 385 | 1.89 | 15 | 1.85 | 0.0201 |
| 5 | New Data | 667 | 2.31 | 32 | 2.21 | |
| 6 | C | 176 | 2.53 | 15 | 2.49 | 0.0468 |
| 6 | New Data | 315 | 2.99 | 33 | 2.86 | |
| 7 | C | 161 | 3.39 | 15 | 3.30 | 0.3027 |
| 7 | New Data | 139 | 3.61 | 29 | 3.50 | |
| 8 | C | 142 | 3.70 | 14 | 3.81 | 0.2111 |
| 8 | New Data | 95 | 4.28 | 24 | 4.16 | |
| 9 | C | 45 | 4.20 | 13 | 4.04 | 0.1117 |
| 9 | New Data | 35 | 4.97 | 15 | 4.96 | |
| 10 | C | 24 | 4.63 | 12 | 4.51 | 0.1529 |
| 10 | New Data | 51 | 5.84 | 13 | 5.69 | |
| 12 | C | 19 | 6.53 | 7 | 5.32 | 0.0455 |
| 12 | New Data | 37 | 7.11 | 12 | 7.70 | |
| 15 | C | 9 | 8.44 | 5 | 7.70 | 0.7228 |
| 15 | New Data | 6 | 8.83 | 4 | 9.13 | |

[1] The Wilcoxon p-value is based on the subject means.

4.0 Oral Pastes 4.1 Misoprostol Oral Paste (10 μg/0.15 g paste). In a stock jar, 20.001 g of ground CYTOTEC® tablets (containing 20.0 mg of misoprostol) was combined with 114.999 g of SUPER WERNET'S® Denture Adhesive Powder. The combination was mixed well by shaking. To the mixture was added 165 g of Base A/C solution. The Base AC solution comprises 5% polyethylene glycol MW 1450 (PEG 1450) and 95% polyethylene glycol MW 300 (PEG 300). The wetted mixture was stirred to break up any lumps and to remove the powder off the side of the container. The mixture was then allowed to set overnight to fully wet. The following morning, the mixture was stirred with a metal spatula to produce 300 g of 0.00667% misoprostol oral paste (10 μg misoprostol/150 mg oral paste). The resulting paste was then dispensed in 10 g aliquots (approximately 8.8 ml) into a 10 ml syringe suitable for oral application. In this embodiment and those that follow, the 150 mg of oral paste corresponds to 0.1275 ml (0.13 ml) of paste in the syringe.

4.2 Misoprostol (0.00667%)/Doxycycline (1%) Oral Paste. In a stock jar, 20.001 g of ground CYTOTEC® tablets (containing 20.0 mg of misoprostol) was combined with 111.999 g of SUPER WERNET'S® Denture Adhesive Powder and 3.0 g of doxycycline. The combination was mixed well by shaking. To the mixture was added 165 g of Base A/C solution (5% PEG 1450:95% PEG 300 wt/wt). The wetted mixture was stirred to break up any lumps and to remove the powder off the side of the container. The mixture was then allowed to set overnight to fully wet. The following morning, the mixture was stirred with a metal spatula to produce 300 g of 0.00667% misoprostol/1% doxycycline oral paste (10 μg misoprostol and 1.5mg doxycycline/150 mg oral paste). The resulting paste was then dispensed in 10 g aliquots (approximately 8.8 ml) into a 10 ml syringe suitable for oral application.

4.3 Misoprostol (0.00667%)/Gentamicin (1%) Oral Paste. In a stock jar, 20.001 g of ground CYTOTEC® tablets (containing 20.0 mg of misoprostol) was combined with 111.999 g of SUPER WERNET'S® Denture Adhesive Powder and 3.0 g of gentamicin. The combination was mixed well by shaking. To the mixture was added 165 g of Base A/C solution (5% PEG 1450:95% PEG 300 wt/wt). The wetted mixture was stirred to break up any lumps and to remove the powder off the side of the container. The mixture was then allowed to set overnight to fully wet. The following morning, the mixture was stirred with a metal spatula to produce 300 g of 0.00667% misoprostol/1% gentamicin oral paste (10 µg misoprostol and 1.5mg gentamicin/150 mg oral paste). The resulting paste was then dispensed in 10 g aliquots (approximately 8.8 ml) into a 10 ml syringe suitable for oral application.

4.4 Misoprostol (0.00667%)/Clarithromycin (1%) Oral Paste. In a stock jar, 20.001 g of ground CYTOTEC® tablets (containing 20.0 mg of misoprostol) was combined with 111.999 g of SUPER WERNET'S® Denture Adhesive Powder and 3.0 g of clarithromycin. The combination was mixed well by shaking. To the mixture was added 165 g of Base A/C solution (5% PEG 1450:95% PEG 300 wt/wt). The wetted mixture was stirred to break up any lumps and to remove the powder off the side of the container. The mixture was then allowed to set overnight to fully wet. The following morning, the mixture was stirred with a metal spatula to produce 300 g of 0.00667% misoprostol/1% clarithromycin oral paste (10 µg misoprostol and 1.5 mg clarithromycin/150 mg oral paste). The resulting paste was then dispensed in 10 g aliquots (approximately 8.8 ml) into a 10 ml syringe suitable for oral application.

4.5 Misoprostol (0.00667%)/Azithromycin (1%) Oral Paste. In a stock jar, 20.001 g of ground CYTOTEC® tablets (containing 20.0 mg of misoprostol) was combined with 111.999 g of SUPER WERNET'S® Denture Adhesive Powder and 3.0 g of azithromycin. The combination was mixed well by shaking. To the mixture was added 165 g of Base A/C solution (5% PEG 1450:95% PEG 300 wt/wt). The wetted mixture was stirred to break up any lumps and to remove the powder off the side of the container. The mixture was then allowed to set overnight to fully wet. The following morning, the mixture was stirred with a metal spatula to produce 300 g of 0.00667% misoprostol/1% azithromycin oral paste (10 µg misoprostol and 1.5 mg azithromycin/150 mg oral paste). The resulting paste was then dispensed in 10 g aliquots (approximately 8.8 ml) into a 10 ml syringe suitable for oral application.

4.6 Misoprostol (0.00667%)/Clindamycin (1%) Oral Paste. In a stock jar, 20.001 g of ground CYTOTEC® tablets (containing 20.0 mg of misoprostol) was combined with 111.999 g of SUPER WERNET'S Denture Adhesive Powder and 3.0 g of clindamycin. The combination was mixed well by shaking. To the mixture was added 165 g of Base A/C solution (5% PEG 1450:95% PEG 300 wt/wt). The wetted mixture was stirred to break up any lumps and to remove the powder off the side of the container. The mixture was then allowed to set overnight to fully wet. The following morning, the mixture was stirred with a metal spatula to produce 300 g of 0.00667% misoprostol/1% clindamycin oral paste (10 µg misoprostol and 1.5 mg clindamycin/150 mg oral paste). The resulting paste was then dispensed in 10 g aliquots (approximately 8.8 ml) into a 10 ml syringe suitable for oral application.

4.7 Misoprostol (0.00667%)/Metronidazole (1%) Oral Paste. In a stock jar, 20.001 g of ground CYTOTEC® tablets (containing 20.0 mg of misoprostol) was combined with 111.999 g of SUPER WERNET'S® Denture Adhesive Powder and 3.0 g of triturated metronidazole. The combination was mixed well by shaking. To the mixture was added 165 g of Base A/C solution (5% PEG 1450:95% PEG 300 wt/wt). The wetted mixture was stirred to break up any lumps and to remove the powder off the side of the container. The mixture was then allowed to set overnight to fully wet. The following morning, the mixture was stirred with a metal spatula to produce 300 g of 0.00667% misoprostol/1% metronidazole oral paste (10 µg misoprostol and 1.5 mg metronidazole/150 mg oral paste). The resulting paste was then dispensed in 10 g aliquots (approximately 8.8 ml) into a 10 ml syringe suitable for oral application.

4.8 Misoprostol (00667%)/Ciprofloxacin (1%) Oral Paste. In a stock jar, 20.001 g of ground CYTOTEC® tablets (containing 20.0 mg of misoprostol) was combined with 111.999 g of SUPER WERNET'S® Denture Adhesive Powder and 3.0 g of ciprofloxacin hydrochloride (ciprofloxacin). The combination was mixed well by shaking. To the mixture was added 165 g of Base A/C solution (5% PEG 1450:95% PEG 300 wt/wt). The wetted mixture was stirred to break up any lumps and to remove the powder off the side of the container. The mixture was then allowed to set overnight to fully wet. The following morning, the mixture was stirred with a metal spatula to produce 300 g of 0.00667% misoprostol/1% ciprofloxacin oral paste (10 µg misoprostol and 1.5 mg ciprofloxacin/150 mg oral paste). The resulting paste was then dispensed in 10 g aliquots (approximately 8.8 ml) into a 10 ml syringe suitable for oral application.

What is claimed is:

1. A pharmaceutical composition comprising in combination:
   (i) a therapeutically effective amount of misoprostol, or a pharmaceutically acceptable acid or salt thereof;
   (ii) an effective amount of doxycycline; and
   (iii) a pharmaceutically acceptable carrier suitable for topical application.

2. The pharmaceutical composition of claim 1, wherein said therapeutically effective amount of misoprostol, or pharmaceutically acceptable acid or salt thereof ranges from about 1 micrograms to about 40 micrograms.

3. The pharmaceutical composition of claim 2, wherein said therapeutically effective amount of misoprostol, or pharmaceutically acceptable acid or salt thereof is within the range of 5 micrograms to 30 micrograms.

4. The pharmaceutical composition of claim 3, wherein said therapeutically effective amount of misoprostol, or pharmaceutically acceptable acid or salt thereof is within the range of 10 micrograms to 20 micrograms.

5. The pharmaceutical composition of claim 4, wherein said therapeutically effective amount of misoprostol, or pharmaceutically acceptable acid or salt thereof is within the range of 10 micrograms to 12 micrograms.

6. The pharmaceutical composition of claim 1, wherein said therapeutically effective misoprostol, or pharmaceutically acceptable acid or salt thereof is in the form of a racemate, enantiomer, or diastereomer.

7. The pharmaceutical composition of claim 1 in oral application form wherein said doxycycline is present in an amount within the range of 0.1% (weight to volume) to 5% (weight to volume).

8. The pharmaceutical composition of claim 7, wherein said doxycycline is present in an amount within the range of 0.1% to 3% (weight to volume).

9. The pharmaceutical composition of claim 8, wherein said doxycycine is present in an amount of 0.1 to 1% (weight to volume).

10. The pharmaceutical composition of claim 1, wherein said misoprostol or a pharmaceutically acceptable acid or salt thereof is misoprostolic acid.

11. The pharmaceutical composition of claim 1, further comprising at least one colloidal dispersion system.

12. The pharmaceutical composition of claim 11, wherein said colloidal dispersion system comprises carbowax.

13. The pharmaceutical composition of claim 1, further comprising at least one additive or preservative.

14. The pharmaceutical composition of claim 13, wherein said additive or preservative comprises polyethylene glycol having an average molecular weight ranging from about 300 MW to about 1450 MW.

15. The pharmaceutical composition of claim 1, further comprising at least one denture adhesive.

16. The pharmaceutical composition of claim 15, wherein said denture adhesive is in powdered form.

17. The pharmaceutical composition of claim 1, wherein said pharmaceutically acceptable carrier is a slow release agent.

18. The pharmaceutical composition of claim 1, wherein said pharmaceutical composition is in the form of a topical or oral formulation.

19. The pharmaceutical composition of claim 18, wherein said topical formulation is an oral paste.

20. A method for treating periodontal disease in a mammalian patient comprising:
  (a) administering to, into, on at or in a periodontal pocket of said patient in need of treatment for periodontal disease a pharmaceutical composition comprising a therapeutically effective amount of misoprostol, or a pharmaceutically acceptable acid or salt thereof in a pharmaceutically acceptable carrier;
  (b) administering to, into, on, at or in a periodontal pocket of said patient an effective amount of a pharmaceutical composition comprising doxycycline;
  (c) optionally, administering to said patient prior to step (a) or step (b) or both, at least one step of sub-gingival scaling, root planning, or curettage;

whereby said periodontal disease in said mammalian patient is ameliorated.

21. The method of claim 20, wherein said mammalian patient is human.

22. The method of claim 20, wherein said mammalian patient is a domesticated animal.

23. A pharmaceutical composition suitable for application to a periodontal surface comprising in combination:
  (i) a therapeutically effective amount of misoprostol, or a pharmaceutically acceptable acid or salt thereof;
  (ii) an effective amount of is doxycycline; and
  (iii) a pharmaceutically acceptable carrier suitable for application to a periodontal surface.

* * * * *

UNITED STATES PATENT AND TRADEMARK OFFICE
CERTIFICATE OF CORRECTION

PATENT NO. : 7,241,746 B2  Page 1 of 1
APPLICATION NO. : 10/635144
DATED : July 10, 2007
INVENTOR(S) : Wingrove and McKee It is certified that error appears in the above-identified patent and that said Letters Patent is hereby corrected as shown below:

At column 34, line 19, delete the word "is" between "an effective amount of" and "doxycycline."

Signed and Sealed this

Sixteenth Day of October, 2007

JON W. DUDAS
*Director of the United States Patent and Trademark Office*